US011337969B2

(12) United States Patent
Arbeit

(10) Patent No.: US 11,337,969 B2
(45) Date of Patent: May 24, 2022

(54) METHODS FOR TREATING CANCER

(71) Applicant: X4 Pharmaceuticals, Inc., Boston, MA (US)

(72) Inventor: Robert D. Arbeit, West Newton, MA (US)

(73) Assignee: X4 Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/091,689

(22) PCT Filed: Apr. 10, 2017

(86) PCT No.: PCT/US2017/026819
§ 371 (c)(1),
(2) Date: Oct. 5, 2018

(87) PCT Pub. No.: WO2017/177230
PCT Pub. Date: Oct. 12, 2017

(65) Prior Publication Data
US 2019/0160051 A1 May 30, 2019

Related U.S. Application Data

(60) Provisional application No. 62/319,857, filed on Apr. 8, 2016.

(51) Int. Cl.
| | | |
|---|---|---|
| *A61K 31/4709* | (2006.01) | |
| *A61P 35/00* | (2006.01) | |
| *A61K 45/06* | (2006.01) | |
| *A61K 39/395* | (2006.01) | |
| *A61K 9/48* | (2006.01) | |
| *A61K 38/17* | (2006.01) | |
| *A61K 39/00* | (2006.01) | |
| *C07K 16/28* | (2006.01) | |

(52) U.S. Cl.
CPC ........ *A61K 31/4709* (2013.01); *A61K 9/4808* (2013.01); *A61K 38/1774* (2013.01); *A61K 39/39558* (2013.01); *A61K 45/06* (2013.01); *A61P 35/00* (2018.01); *C07K 16/2818* (2013.01); *A61K 9/485* (2013.01); *A61K 9/4866* (2013.01); *A61K 2039/505* (2013.01)

(58) Field of Classification Search
CPC .............................. A61K 31/47; A61K 31/4184
See application file for complete search history.

(56) References Cited

U.S. PATENT DOCUMENTS

| | | |
|---|---|---|
| 4,933,447 A | 6/1990 | Konno et al. |
| 5,021,409 A | 6/1991 | Murrer et al. |
| 5,235,056 A | 8/1993 | Cunkle et al. |
| 5,563,151 A | 10/1996 | Bowles et al. |
| 5,582,823 A | 12/1996 | Souza et al. |
| 5,583,131 A | 12/1996 | Bridger et al. |
| 5,698,546 A | 12/1997 | Bridger et al. |
| 5,817,807 A | 10/1998 | Bridger et al. |
| 5,932,749 A | 8/1999 | Li et al. |
| 6,001,826 A | 12/1999 | Murrer et al. |
| 6,245,799 B1 | 6/2001 | Asselin et al. |
| 6,268,354 B1 | 7/2001 | Nishimura et al. |
| 6,365,583 B1 | 4/2002 | MacFarland et al. |
| 6,506,770 B1 | 1/2003 | Bridger et al. |
| 6,552,065 B2 | 4/2003 | Remiszewski et al. |
| 6,635,278 B1 | 10/2003 | Dahl et al. |
| 6,683,192 B2 | 1/2004 | Bax |
| 6,734,191 B2 | 5/2004 | Bridger et al. |
| 6,734,194 B2 | 5/2004 | End et al. |
| 6,794,379 B2 | 9/2004 | Medina et al. |
| 6,825,351 B2 | 11/2004 | McEachern et al. |
| 6,835,731 B2 | 12/2004 | Bridger et al. |
| 6,864,265 B2 | 3/2005 | Bridger et al. |
| 6,878,714 B2 | 4/2005 | Askew et al. |
| 6,987,102 B2 | 1/2006 | Bridger et al. |
| 7,053,215 B2 | 5/2006 | Medina et al. |
| 7,071,189 B2 | 7/2006 | Kawashima et al. |
| 7,091,217 B2 | 8/2006 | Bridger et al. |
| 7,135,570 B2 | 11/2006 | McEachern et al. |
| 7,169,750 B2 | 1/2007 | Bridger et al. |
| 7,291,631 B2 | 11/2007 | Bridger et al. |
| 7,332,605 B2 | 2/2008 | Crawford et al. |
| 7,354,932 B2 | 4/2008 | Bridger et al. |

(Continued)

FOREIGN PATENT DOCUMENTS

| | | |
|---|---|---|
| EP | 0434385 | 6/1991 |
| WO | WO-1997009976 | 3/1997 |

(Continued)

OTHER PUBLICATIONS

X4P-001 Product Page. Adis Insight. Published Mar. 20, 2019 (Year: 2019).*
Motzer et al., (J. Clin. Oncology vol. 33 pp. 1430-1437 published 2014). (Year: 2014).*
Hainsworth (Targeted Oncology vol. 11 p. 643-653. Published 2016 (Year: 2016).*
Portella (PLOSOne vol. 8 p. e74548 pp. 1-8 published 2013) (Year: 2013).*
Choueiri et al (NEJM vol. 376 pp. 354-366 published 2017) (Year: 2017).*
Raman et al (Biomed Research International vol. 2015 published Mar. 2015). (Year: 2015).*

(Continued)

*Primary Examiner* — Theodore R. Howell
*Assistant Examiner* — George W Kosturko
(74) *Attorney, Agent, or Firm* — Andrea L. C. Reid; Joseph W. Arico; Dechert LLP

(57) ABSTRACT

The present invention relates to methods of treating patients with advanced forms of cancer, such as unresectable or metastatic renal cell carcinoma or kidney cancer, in which X4P-001 or a pharmaceutically acceptable salt thereof is administered as monotherapy or in combination with an immune checkpoint inhibitor, such as nivolumab. The methods demonstrate surprising results, including regression of disease, with comparatively little toxicity.

23 Claims, No Drawings

(56) References Cited

U.S. PATENT DOCUMENTS

| | | | |
|---|---|---|---|
| 7,354,934 B2 | 4/2008 | Bridger et al. | |
| 7,390,799 B2 | 6/2008 | Bruncko et al. | |
| 7,452,994 B2 | 11/2008 | McEachern et al. | |
| 7,491,544 B2 | 2/2009 | Canary et al. | |
| 7,501,518 B2 | 3/2009 | Chen et al. | |
| 7,550,484 B2 | 6/2009 | Bridger et al. | |
| 7,592,351 B2 | 9/2009 | Sundermann et al. | |
| 7,723,525 B2 | 5/2010 | Crawford et al. | |
| 7,863,293 B2 | 1/2011 | Bridger et al. | |
| 7,897,590 B2 | 3/2011 | Bridger et al. | |
| 7,935,692 B2 | 5/2011 | Bridger et al. | |
| 8,138,347 B2 | 3/2012 | Knight et al. | |
| 8,168,783 B2 | 5/2012 | Kokubo et al. | |
| 8,178,123 B2 | 5/2012 | Pauletti et al. | |
| 8,778,967 B2 | 7/2014 | Bridger et al. | |
| 8,889,159 B2 | 11/2014 | Cleary et al. | |
| 8,906,682 B2 | 12/2014 | June et al. | |
| 9,119,790 B2 | 9/2015 | Crowley et al. | |
| 9,155,723 B2 | 10/2015 | Jain et al. | |
| 9,267,934 B2 | 2/2016 | Singh et al. | |
| 9,314,468 B2 | 4/2016 | Clark et al. | |
| 9,353,086 B2 | 5/2016 | Savory et al. | |
| 10,548,889 B1 | 2/2020 | Brands | |
| 10,610,527 B2 | 4/2020 | Arbeit et al. | |
| 10,759,796 B2 | 9/2020 | Bourque et al. | |
| 10,953,003 B2 * | 3/2021 | Ragan | A61K 9/4866 |
| 11,045,461 B2 | 6/2021 | Brands | |
| 2003/0220341 A1 | 11/2003 | Bridger et al. | |
| 2003/0232808 A1 | 12/2003 | Kobayashi et al. | |
| 2005/0154201 A1 | 7/2005 | Chen et al. | |
| 2005/0227958 A1 | 10/2005 | Wang et al. | |
| 2007/0123538 A1 | 5/2007 | Dunkle et al. | |
| 2007/0167459 A1 | 7/2007 | Habashita et al. | |
| 2007/0232615 A1 | 10/2007 | Gudmundsson et al. | |
| 2008/0045537 A1 | 2/2008 | Gudmundsson et al. | |
| 2008/0058353 A1 | 3/2008 | Banks | |
| 2008/0096861 A1 | 4/2008 | Gudmundsson et al. | |
| 2008/0167341 A1 | 7/2008 | Bridger et al. | |
| 2008/0171740 A1 | 7/2008 | Gudmundsson et al. | |
| 2009/0093454 A1 | 4/2009 | Gudmundsson et al. | |
| 2009/0203533 A1 | 8/2009 | Munnes et al. | |
| 2009/0247570 A1 | 10/2009 | Mayer | |
| 2009/0325877 A1 | 12/2009 | Grunt et al. | |
| 2010/0002272 A1 | 1/2010 | Sato et al. | |
| 2010/0022724 A1 | 1/2010 | Jacobsen et al. | |
| 2010/0028299 A1 | 2/2010 | Einav et al. | |
| 2010/0143301 A1 | 6/2010 | Desai et al. | |
| 2011/0206607 A1 | 8/2011 | Olsson et al. | |
| 2011/0293521 A1 | 12/2011 | Hyde et al. | |
| 2012/0041028 A1 | 2/2012 | Cooper et al. | |
| 2012/0141471 A1 | 6/2012 | Salvino et al. | |
| 2013/0216531 A1 | 8/2013 | Jain et al. | |
| 2014/0170677 A1 | 6/2014 | Klinguer-Hamour et al. | |
| 2014/0275260 A1 | 9/2014 | Kawale et al. | |
| 2015/0004239 A1 | 1/2015 | Cullen et al. | |
| 2015/0030561 A1 | 1/2015 | Dale et al. | |
| 2015/0037328 A1 | 2/2015 | Liu et al. | |
| 2015/0216843 A1 | 8/2015 | Fearon | |
| 2015/0246019 A1 | 9/2015 | Bridger et al. | |
| 2015/0301058 A1 | 10/2015 | Schettini et al. | |
| 2015/0352208 A1 * | 12/2015 | Fearon | A61K 31/713 424/174.1 |
| 2016/0089385 A1 | 3/2016 | Sherman et al. | |
| 2016/0222465 A1 | 8/2016 | Treon et al. | |
| 2016/0228413 A1 | 8/2016 | Bridger et al. | |
| 2017/0090658 A1 | 3/2017 | Park et al. | |
| 2017/0166591 A1 | 6/2017 | Ojima et al. | |
| 2017/0234879 A1 | 8/2017 | Klinguer-Hamour et al. | |
| 2017/0333436 A1 | 11/2017 | Treon et al. | |
| 2018/0228894 A1 * | 8/2018 | Fearon | A61K 31/7028 |
| 2018/0369167 A1 | 12/2018 | Arbeit et al. | |
| 2018/0369229 A1 | 12/2018 | Ragan et al. | |
| 2019/0030023 A1 | 1/2019 | Arbeit et al. | |
| 2019/0083485 A1 | 3/2019 | Arbeit et al. | |
| 2019/0322671 A1 | 10/2019 | Bourque et al. | |
| 2020/0123150 A1 | 4/2020 | Bourque et al. | |
| 2020/0138804 A1 | 5/2020 | Parasuraman et al. | |
| 2020/0253953 A1 | 8/2020 | Brands | |
| 2020/0255414 A1 | 8/2020 | Bourque et al. | |
| 2020/0268739 A1 | 8/2020 | Arbeit et al. | |
| 2021/0025895 A1 | 1/2021 | Wang et al. | |

FOREIGN PATENT DOCUMENTS

| | | | |
|---|---|---|---|
| WO | WO-1999004794 | 2/1999 | |
| WO | WO-1999031264 | 6/1999 | |
| WO | WO-2000002870 | 1/2000 | |
| WO | WO-2000022599 | 4/2000 | |
| WO | WO-2000045814 | 8/2000 | |
| WO | WO-2000056729 | 9/2000 | |
| WO | 2001042241 A1 | 6/2001 | |
| WO | WO-2002022600 | 3/2002 | |
| WO | WO-2002034745 | 5/2002 | |
| WO | WO-2002076948 | 10/2002 | |
| WO | 02088112 A1 | 11/2002 | |
| WO | WO-2003011277 | 2/2003 | |
| WO | WO-2003055876 | 7/2003 | |
| WO | 2003063794 A2 | 8/2003 | |
| WO | WO-2004019973 | 3/2004 | |
| WO | 2004089925 A1 | 10/2004 | |
| WO | 2004093817 | 11/2004 | |
| WO | 2004106328 A1 | 12/2004 | |
| WO | WO-2004106493 | 12/2004 | |
| WO | 2005007623 A2 | 1/2005 | |
| WO | 2005113554 A2 | 12/2005 | |
| WO | WO-2006026703 | 3/2006 | |
| WO | WO-2006036816 | 4/2006 | |
| WO | 2006078846 A1 | 7/2006 | |
| WO | WO-2006096444 | 9/2006 | |
| WO | 2006122806 A2 | 11/2006 | |
| WO | WO-2006138259 | 12/2006 | |
| WO | 2007008539 | 1/2007 | |
| WO | 2007016176 A2 | 2/2007 | |
| WO | 2007022523 A2 | 2/2007 | |
| WO | WO-2007027999 | 3/2007 | |
| WO | 2007044729 A2 | 4/2007 | |
| WO | 2007053452 A1 | 5/2007 | |
| WO | 2007070514 A1 | 6/2007 | |
| WO | 2007084786 A1 | 7/2007 | |
| WO | 2007087548 | 8/2007 | |
| WO | WO-2007087549 | 8/2007 | |
| WO | 2007129161 A2 | 11/2007 | |
| WO | 2008039218 A2 | 4/2008 | |
| WO | 2008109943 A1 | 9/2008 | |
| WO | 2008118802 A1 | 10/2008 | |
| WO | WO-2009026251 | 2/2009 | |
| WO | 2009114512 A1 | 9/2009 | |
| WO | 2009117706 A2 | 9/2009 | |
| WO | 2009117710 | 9/2009 | |
| WO | 2010019239 A2 | 2/2010 | |
| WO | 2010086185 A1 | 8/2010 | |
| WO | 2011090760 A1 | 7/2011 | |
| WO | 2011147026 | 12/2011 | |
| WO | WO-2011147026 A2 * | 12/2011 | A61K 31/4184 |
| WO | 2012049277 | 4/2012 | |
| WO | WO-2012075362 | 6/2012 | |
| WO | 2012094703 | 7/2012 | |
| WO | WO-2012094703 A1 * | 7/2012 | A61P 13/12 |
| WO | 2013017566 A1 | 2/2013 | |
| WO | 201503887 A1 | 1/2015 | |
| WO | WO-2015030853 | 3/2015 | |
| WO | WO-2015038887 | 3/2015 | |
| WO | WO-2015069770 | 5/2015 | |
| WO | 2015134605 A1 | 9/2015 | |
| WO | WO-2015143012 | 9/2015 | |
| WO | 2015200341 A1 | 12/2015 | |
| WO | WO-2016008976 | 1/2016 | |
| WO | 2016089872 A1 | 6/2016 | |
| WO | 2016090434 A1 | 6/2016 | |
| WO | 2016094377 A1 | 6/2016 | |
| WO | 2016146261 A1 | 9/2016 | |
| WO | WO-2016201425 | 12/2016 | |
| WO | 2017048702 A1 | 3/2017 | |
| WO | WO-2017106328 | 6/2017 | |

(56) References Cited

FOREIGN PATENT DOCUMENTS

| WO | WO-2017106332 | | 6/2017 |
|---|---|---|---|
| WO | WO-2017112894 | | 6/2017 |
| WO | WO-2017127811 | | 7/2017 |
| WO | 2017181073 | A1 | 10/2017 |
| WO | 2017223229 | A1 | 12/2017 |
| WO | 2017223239 | A1 | 12/2017 |
| WO | 2017223243 | A1 | 12/2017 |
| WO | WO-2018237158 | | 12/2018 |
| WO | 2019094392 | A1 | 5/2019 |
| WO | 2019126106 | A1 | 6/2019 |
| WO | 2019200223 | A1 | 10/2019 |
| WO | 2020047410 | A1 | 3/2020 |
| WO | 2021127496 | A1 | 6/2021 |
| WO | 2021183650 | A1 | 9/2021 |

OTHER PUBLICATIONS

Motzer (J. Clin. Oncology vol. 33 pp. 1430-1437 published 2014), (Year: 2014).*
D'Alterio (Cell Cycle vol. 9 p. 4492-4500 (2010), (Year: 2010).*
O'Boyle (British Journal of Cancer vol. 108 pp. 1634-1640. Published 2013), (Year: 2013).*
Reagan-Shaw et al (FASEBJ vol. 22 pp. 659-661. Published 2007) (Year: 2007).*
Langan et al (Journal of Cancer vol. 3 pp. 184-190, published 2012) (Year: 2012).*
Stone et al (Antimicrobial Agents and Chemotherapy vol. 51 pp. 2351-2358 published 2007 (Year: 2007).*
"Common Terminology Criteria for Adverse Events (CTCAE), Version 4.0," U.S. Department of Health and Human Services, National Institutes of Health, National Cancer Institute, NIH Publication No. 09-5410, May 28, 2009, revised Jun. 2010 (196 pages).
"European Medicines Agency, Background Review for Sodium Laurilsulfate Used as an Excipient," Jul. 23, 2015, http://www.ema.europa.eu/docs/en_GB/document library/Report/2015/08/WC500191475.pdf. page 5, table 1. Date Accessed Jan. 23, 2017 (18 pages).
"Nivolumab," Drugbank, http://www.drugbank.ca/drugs/DB09035. Date Accessed, Nov. 30, 2018 (14 pages).
"Q3C—Tables and Lists, Guidance for Industry," U.S. Department of Health and Human Services, Food and Drug Adminstration, Center for Drug Evaluation and Research, Center for Biologies Evaluation and Research, Aug. 2018, https://www.fda.gov/downloads/Drugs/GuidanceComplianceRegulatoryInformation/Guidances/UCM073395.pdf. Date Accessed Jan. 22, 2019 (10 pages).
"Therapeutics," Encyclopedia Britannica Online, 2018, https://www.britannica.com/science/therapeutics. Date Accessed, Nov. 6, 2018 (1 page).
"WMA Declaration of Helsinki—Ethical Principles for Medical Research Involving Human Subjects," amended Oct. 2013, http://www.wma.net/en/30publications/10policies/b3/. Date Accessed Apr. 6, 2015 (4 Pages).
Abi-Younes et al., "The Stromal Cell-Derived Factor-1 Chemokine is a Potent Platelet Agonist Highly Expressed in Atherosclerotic Plaques," Circulation Research, vol. 86, Feb. 4, 2000 (pp. 131-138).
Acharyya et al.," CXCL1 paracrine network links cancer chemoresistance and metastasis." Cell, vol. 150, No. 1, 2012 (pp. 165-178).
Aduro Biotech, Inc., "Safety and Efficacy of MIW815 (ADU-S100) +/−Ipilimumab in Patients With Advanced/Metastatic Solid Tumors or Lymphomas," ClinicalTrials.gov: NCT02675439, First Posted: Feb. 5, 2016, Last Update: Sep. 26, 2018, https://clinicaltrials.gov/ct2/show/study/NCT02675439. Date Accessed, Mar. 18, 2019 (6 pages).
Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).

Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).
Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).
Aileron Therapeutics, " ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).
Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).
ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).
Ami and Horui, "Lipase-catalyzed Kinetic Resolution of (±)-trans and cis-2-Azidocycloalkanols," Bioscience, Biotechnology, Biochemistry, vol. 63, No. 12, 1999 (pp. 2150-2156).
An et al., "Solution phase combinatorial chemistry. Discovery of 13- and 15-membered polyazapyridinocyclophane libraries with antibacterial activity," Tetrahedron, vol. 54, (pp. 3999-4012).
Arenburg et al., "The role of CXC chemokines in the regulation of angiogenesis in non-small cell lung cancer," Journal of Leukocyte Biology, vol. 62, 1997 (pp. 554-562).
Auiti et al., "The Chemokine SDF-1 is a Chemoattractant for Human CD34+ Hematopoietic Progenitor Cells and Provides a New Mechanism to Explain the Mobilization of CD34+ Progenitors to Peripheral Blood," Journal of Experimental Medicine, vol. 185, No. 1, Jan. 6, 1997 (pp. 111-120).
Ayers et al., "IFN-y-related mRNA profile predicts clinical response to PD-1 blockade," The Journal of Clinical Investigation, vol. 127, No. 8, 2017 (pp. 2930-2940).
Baggiolini, "Chemokines and leukocyte traffic," Nature, vol. 392, Apr. 9, 1998 (pp. 565-568).
Balabanian, et al., "Proper desensitization of CXCR4 is required for lymphocyte development and peripheral compartmentalization in mice," Blood, vol. 119, No. 24, Mar. 2012 (pp. 5722-5730).
Balabanian, et al., "WHIM syndromes with different genetic anomalies are accounted for by impaired CXCR4 desensitization to CXCL12," Blood, vol. 105, No. 6, Mar. 15, 2005 (pp. 2449-2457).
Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).
Beaussant-Cohen, et al., "Description and outcome of a cohort of 8 patients with WHIM syndrome from the French Severe Chronic Neutropenia Registry," Orphanet Journal of Rare Diseases, vol. 7, No. 71, Jun. 14, 2012 (pp. 5722-5730).
Berge et al., "Pharmaceutical Salts," Journal of Pharmaceutical Sciences, vol. 66, No. 1, Jan. 1977 (pp. 1-19).
Blaak et al., "In vivo HIV-1 infection of CD45RA+CD4+ T cells is established primarily by syncytium-inducing variants and correlates with the rate of CD4+ T cell decline," Proceedings of the National Academy of Sciences of the United States of America, vol. 97, No. 3, 2000 (pp. 1269-1274).
Blanchette, S., "NCT02823405: X4P-001 and Prembrolizumab in Patents With Advanced Melanoma (X4P-001-MELA)," Jul. 6, 2016, https://clinicaltrials.gov/ct2/show/NCT02823405> Date Accessed Oct. 5, 2018 (7 pages).
Blanco et al. "The CXCR4 Antagonist AMD3100 Efficiently Inhibits Cell-Surface-Expressed Human Immunodeficiency Virus Type 1

(56) References Cited

OTHER PUBLICATIONS

Envelope-Induced Apoptosis," Antimicrobial Agents and Chemotherapy, vol. 44, No. 1., Jan. 2000 (pp. 51-56).
Bleul et al., "B Lymphocyte Chemotaxis Regulated in Association with Microanatomic Localization, Differentiation State, and B Cell Receptor Engagement," Journal of Experimental Medicine, vol. 187, No. 5, Mar. 2, 1998 (pp. 753-762).
Bohinjec, "Myelokathexis: chronic neutropenia with hyperplastic bone marrow and hypersegmented neutrophils in two siblings," Blut, vol. 42, 1981 (pp. 191-196).
Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).
Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update: Jan. 31, 2019, https://clinicaltrials.gov/ct2/show/study/NCT02737475. Date Accessed, Mar. 18, 2019 (11 pages).
Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).
Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).
Bristol-Myers Squibb, "An Investigational Immuno-therapy Study to Evaluate the Safety and Effectiveness of Experimental Medication BMS-986207 by Itself and in Combination With Nivolumab in Solid Cancers That are Advanced or Have Spread," ClinicalTrials.gov: NCT02913313, First Posted: Sep. 23, 2016, Last Update: Jan. 31, 2019, https://clinicaltrials.gov/ct2/show/study/NCT02913313. Date Accessed, Mar. 25, 2019 (9 pages).
Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).
Broxmeyer et al., "Effects of in vivo treatment with PIXY321 (GM-CSF/IL-3 fusion protein) on proliferation kinetics of bone marrow and blood myeloid progenitor cells in patients with sarcoma," Experimental Hematology, vol. 23, 1995 (pp. 335-340).
Broxmeyer, "A Whim satisfactorily addressed," Blood, vol. 123, No. 15, 2014 (pp. 2286-2288).
Burger et al., "Chronic Lymphocytic Leukemia B Cells Express Functional CXCR4 Chemokine Receptors That Mediate Spontaneous Migration Beneath Bone Marrow Stromal Cells," Blood, vol. 94, No. 11, Dec. 1, 1999 (pp. 3658-3667).
Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).
Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).
Cao, et al., "Effect of Low-Dose Ritonavir on the Pharmacokinetics of the CXCR4 Antagonist AMD070 in Healthy Volunteers," Antimicrobial Agents and Chemotherpy, vol. 52, No. 5, 2008 (pp. 1630-1634).
Catalano, J. G. et al., "Synthesis of a novel tricyclic 1, 2,3,4, 4a, 5,, 10b-octahydro-1, 10-phenanthroline ring system and CXCR4 antagonists with potent activity against HIV-1," Bioorganic & Medicinal Chemistry Letters, vol. 20, 2010 (pp. 2186-2190).
Celgene, "A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).
Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).
Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).
Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update: Jan. 7, 2019, https://clinicaltrials.gov/ct2/show/study/NCT02335918. Date Accessed, Mar. 18, 2019 (9 pages).
Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update: Jan. 31, 2018, https://clinicaltrials.gov/ct2/show/study/NCT01460134. Date Accessed, Mar. 18, 2019 (9 pages).
Centre Leon Berard, "Evaluation of Safety and Activity of an Anti-PDL 1 Antibody (DURVALUMAB) Combined With CSF-1R Tki (Pexidartinib) in Patients With Metastatic/Advanced Pancreatic or Colorectal Cancers (MEDIPLEX)," ClinicalTrials.gov: NCT02777710, First Posted: May 19, 2016, Last Update: Jan. 17, 2019, https://clinicaltrials.gov/ct2/show/study/NCT02777710. Date Accessed, Mar. 18, 2019 (10 pages).
Chen et al., "CXCR4 inhibition in tumor microenvironmental facilitates anti-programmed death receptor-1 immunotherapy in sorafenib-treated hepatocellular carcinoma in mice," Hepatology, vol. 61, No. 5, May 2015, (pp. 1591-1602).
Clark, PE., "Rationale for targeted therapies and potential role of pazopanib in advanced renal cell carcinoma," Biologies: Targets and Therapy, vol. 4, Jun. 26, 2010 (pp. 187-197).
Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).
Comba et al., "Catalytic Aziridination of Styrene with Copper Complexes for Substituted 3,7-Diazabicyclo[3.3.1]nonanones," European Journal of Inorganic Chemistry, vol. 9, 2003 (pp. 1711-1718).
Connolly et al., "Complexities of TGF-β Targeted Cancer Therapy," (2012) International Journal of Biological Sciences vol. 8, No. 7, Jul. 2012 (pp. 964-978).
Connor et al., "Human Immunodeficiency Virus Type 1 Variants with Increased Replicative Capacity Develop during the Asymptomatic Stage before Disease Progression," Journal of Virology, vol. 68, No. 7, 1994 (pp. 4400-4408).
Crawford et al., " AMD070, a CXCR4 Chemokine Receptor Antagonist: Practical Large-Scale Laboratory Synthesis," Organic Process Research and Development, vol. 12, No. 5, 2008 (pp. 823-830).

(56) References Cited

OTHER PUBLICATIONS

Crump et al., "Solution structure and basis for functional activity of stromal cell derived factor-1; dissociation of CXCR4 activation from binding and inhibition of HIV-1," The EMBO Journal, vol. 16, No. 23, 1997 (pp. 6996-7007).
D'Alterio, et al., "Inhibition of stromal CXCR4 impairs development of lung metastases," Cancer Immunology, Immunotherapy, vol. 61, 2012 (pp. 1713-1720).
Dale et al., "Effects of Granulocyte-Macrophage Colony-Stimulating Factor (GM-CSF) on Neutrophil Kinetics and Function in Normal Human Volunteers," American Journal of Hematology, (1998), vol. 57, 1998 (pp. 7-15).
Dale et al., "The CXCR4 antagonist plerixafor is a potential therapy for myelokathexis, WHIM syndrome," Blood, vol. 118, No. 18, Nov. 3, 2011 (pp. 4963-4966).
Dale et al., "The Severe Chronic Neutropenia International Registry: 10-Year Follow-up Report," Supportive Cancer Therapy, vol. 3, No. 4, 2006 (pp. 220-231).
Dana-Farber Cancer Institute, "LY3022855 With BRAF/MEK Inhibition in Patients With Melanoma," ClinicalTrials.gov: NCT03101254, First Posted: Apr. 5, 2017, Last Update: Feb. 4, 2019, https://clinicaltrials.gov/ct2/show/study/NCT03101254. Date Accessed, Mar. 18, 2019 (9 pages).
Debnath et al., "Small molecule inhibitors of CXCR4," Theranostics, vol. 3, No. 1, Jan. 15, 2013 (pp. 47-75).
Doranz, "Chemokine receptors as fusion cofactors for human immunodeficiency virus type 1 (HIV-1)," Immunologic Research, vol. 16, 1997 (pp. 15-28).
Dorwald, "Side Reactions in Organic Synthesis," Wiley: VCH, Weinheim, 2005 (p. IX of preface and pp. 1-15, 41).
Dotta et al., "Clinical and genetic features of warts, hypogammaglobulinemia, infections and myelokathexis (WHIM) syndrome," Current Molecular Medicine, vol. 11, 2011 (pp. 317-325).
Duda et al., "CXCL12 (SDFla)-CXCR4/CXCR7 Pathway Inhibition: An Emerging Sensitizer for Anticancer Therapies?," Clinical Cancer Research, vol. 17, No. 8, 2011 (pp. 2074-2080).
Egberink et al., "Bicyclams, Selective Antagonists of the Human Chemokine Receptor CXCR4, Potently Inhibit Feline Immunodeficiency Virus Replication," Journal of Virology, vol. 73, No. 8, 1999 (pp. 6346-6352).
Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update: Jan. 15, 2019, https://clinicaltrials.gov/ct2/show/study/NCT02718911. Date Accessed, Mar. 18, 2019 (7 pages).
Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).
EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).
Facciabene et al., "Tumour hypoxia promotes tolerance and angiogenesis via CCL28 and Treg cells," Nature, vol. 475, 2011 (pp. 226-230).
Fedyk et al., "Maturation decreases responsiveness of human bone marrow B lineage cells to stromal-derived factor 1 (SDF-1)," Journal of Leukocyte Biology, vol. 66, Oct. 1999 (pp. 667-673).
Feig et al., "Targeting CXCL12 from FAP-expressing carcinoma-associated fibroblasts synergizes with anti-PD-L1 immunotherapy in pancreatic cancer," PNAS, vol. 110, No. 50, 2013 (p. 20212-20217).
Finke J. et al., "MDSC as a mechanism of tumor escape from sunitinib mediated anti-angiogenic therapy," International Immunopharmacology, vol. 11, No. 7, Jul. 2011 (pp. 856-861).
Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).
Forty Seven, Inc., "Trial of Hu5F9-G4 in Combination With Cetuximab in Patients With Solid Tumors and Advanced Colorectal Cancer," ClinicalTrials.gov: NCT02953782, First Posted: Nov. 3, 2016, Last Update: Aug. 1, 2018, https://clinicaltrials.gov/ct2/show/study/NCT02953782. Date Accessed, Mar. 18, 2019 (7 pages).
Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).
Gacche, RN. "Compensatory angiogenesis and tumor refractoriness," Oncogenesis, vol. 4, e153, Jun. 1, 2015 (8 pages).
Gale et al., "Chemokines: extracellular messengers for all occasions?," BioEssays, vol. 21, 1999 (pp. 17-28).
Galsky et al., "A Phase I Trial of LY2510924, a CXCR4 Peptide Antagonist, in Patients with Advanced Cancer," Clinical Cancer Research, vol. 20, No. 16, Aug. 15, 2014 (pp. 3581-3588; 4414).
Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).
Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).
Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).
Glaspy et al., "Peripheral Blood Progenitor Cell Mobilization Using Stem Cell Factor in Combination With Filgrastim in Breast Cancer Patients," Blood, vol. 90, 1997 (pp. 2939-2951).
GlaxoSmithKline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).
GlaxoSmithKline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).
Gonzalo et al., "Critical Involvement of the Chemotactic Axis CXCR4/Stromal Cell-Derived Factor-1α in the Inflammatory Component of Allergic Airway Disease," Journal of Immunology, vol. 165, No. 1, Jul. 1, 2000 (pp. 499-508).
Gudmundsson, K.S., "Amine sustitutedN-(1H-benzimidazol-2ylmethyl)-5,6,7,8-tetrahydro-8-quino-linamines as CXCR4 antagonists with potent activity against HIV-1," Bioorganic & Medicinal Chemistry Letters, 2009 (pp. 1-5).
Gulino et al., "Altered leukocyte response to CXCL12 in patients with warts hypogammaglobulinemia, infections, myelokathexis (WHIM) syndrome," Blood, vol. 104, No. 2, 2014 (pp. 444-452).
H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted: Jan. 11, 2016, Last Update: Dec. 4, 2018, https://clinicaltrials.gov/ct2/show/study/NCT02652455. Date Accessed, Mar. 18, 2019 (9 pages).
Hendrix et al., "Pharmacokinetics and safety of AMD-3100, a novel antagonist of the CXCR-4 chemokine receptor, in human volunteers," Antimicrobial Agents and Chemotherapy, vol. 44, No. 6, Jun. 2000 (pp. 1667-1673).
Hendrix, et al., "Safety, Pharmacokinetics, and Antiviral Activity of AMD3100, a Selective CXCR4 Receptor Inhibitor, in HIV-1 Infection," Journal of Acquired Immune Deficiency Syndrome, vol. 37, No. 2. Oct. 1, 2004 (pp. 1253-1262).

(56) References Cited

OTHER PUBLICATIONS

Hernandez et al., "Mutations in the chemokine receptor gene CXCR4 are associated with WHIM syndrome, a combined immunodeficiency disease," Nature Genetics, vol. 34, No. 1., May 31, 2003 (pp. 70-74).
Hesselgesser et al., "CD-4-independent association between HIV-1 gpl20 and CXCR4: functional chemokine receptors are expressed in human neurons," Current Biology, vol. 7, No. 2, Jan. 21, 1997 (pp. 112-121).
Hesselgesser et al., "Neuronal apoptosis inducted by HIV-1 gp120 and chemokine SDF-1α mediated by the chemokine receptor CXCR4," Current Biology, vol. 8, No. 10, Apr. 27, 1998 (pp. 595-598).
Highfill et al., "Disruption of CXCR2-mediated MDSC tumor trafficking enhances anti-PD1 efficacy," Science Translational Medicine, vol. 6, No. 237, May 21, 2014 (pp. 1-13).
Husain Z. et al., "Tumor-derived lactate modifies antitumor immune response: Effect on myeloid-derived suppressor cells and NK cells," Journal of Immunology, vol. 191, 2013 (pp. 1486-1495).
Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update: Jan. 11, 2019, https://clinicaltrials.gov/ct2/show/study/NCT02676869. Date Accessed, Mar. 25, 2019 (6 pages).
Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).
Immutep S.A., "IMP321 Plus First-line Paclitaxel in Metastatic Breast Carcinoma," ClinicalTrials.gov: NCT00349934, First Posted: Jul. 10, 2006, Last Update: Jan. 7, 2010, https://clinicaltrials.gov/ct2/show/study/NCT00349934. Date Accessed, Mar. 25, 2019 (7 pages).
Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).
Incyte Biosciences International Sàrl, "Phase ½ Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).
Innate Pharma, "Combination Study of IPH2201 With Ibrutinib in Patients With Relapsed, Refractory or Previously Untreated Chronic Lymphocytic Leukemia," ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).
Innate Pharma, "Efficacy Study of Anti-KIR Monoclonal Antibody as Maintenance Treatment in Acute Myeloid Leukemia (EFFIKIR) (EFFIKIR)," ClinicalTrials.gov: NCT01687387, First Posted: Sep. 18, 2012, Last Update: Feb. 8, 2019, https://clinicaltrials.gov/ct2/show/study/NCT01687387. Date Accessed, Mar. 18, 2019 (9 pages).
Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).
Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).
Innate Pharma, "Study on the Anti-tumor Activity, Safety and Pharmacology of IPH2101 in Patients With Smoldering Multiple Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).
Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).
International Preliminary Examination Report for PCT/US2002/041407, titled "Chemokine Receptor Binding Heterocyclic Compounds with Enhanced Efficacy," dated Aug. 1, 2003 (4 pages).
International Preliminary Report on Patentability for PCT/US2004/015977, titled "Chemokine Receptor Binding Heterocyclic Compounds with Enhanced Efficacy," dated May 2, 2006 (4 pages).
International Search Report and Written Opinion issued by the United States Patent and Trademark Office as International Searching Authority for International Patent Application No. PCT/US2016/066634, dated Feb. 16, 2017 (15 pages).
International Search Report and Written Opinion issued by the United States Patent and Trademark Office as International Searching Authority for International Patent Application No. PCT/US2016/066639, dated Feb. 16, 2017 (11 pages).
International Search Report and Written Opinion issued by the United States Patent and Trademark Office as International Searching Authority for International Patent Application No. PCT/US2016/068394, dated Mar. 3, 2017 (10 pages).
International Search Report and Written Opinion issued by the United States Patent and Trademark Office as International Searching Authority for International Patent Application No. PCT/US2017/014578, dated Apr. 4, 2017 (12 pages).
International Search Report and Written Opinion issued by the United States Patent and Trademark Office as International Searching Authority for International Patent Application No. PCT/US2018/066141, dated Mar. 8, 2019 (8 pages).
International Search Report issued by the United States Patent and Trademark Office as International Searching Authority for International Patent Application No. PCT/US05/34491, dated Apr. 11, 2006 (2 pages).
International Search Report issued by the United States Patent and Trademark Office as International Searching Authority for International Patent Application No. PCT/US05/34950, dated Oct. 4, 2006 (4 pages).
International Search Report issued by the United States Patent and Trademark Office as International Searching Authority for International Patent Application No. PCT/US2002/029372, dated Aug. 10, 2004 (4 pages).
International Search Report issued by the United States Patent and Trademark Office as International Searching Authority for International Patent Application No. PCT/US2004/011328, dated Oct. 20, 2004 (2 pages).
International Search Report issued by the United States Patent and Trademark Office as International Searching Authority for International Patent Application No. PCT/US2004/012627, dated Jan. 13, 2005 (3 pages).
International Search Report issued by the United States Patent and Trademark Office as International Searching Authority for International Patent Application No. PCT/US2004/015977, dated Jul. 15, 2005 (3 pages).
International Search Report issued by the United States Patent and Trademark Office as International Searching Authority for International Patent Application No. PCT/US2005/08268, dated May 26, 2005 (3 pages).
Ishii et al., "Expression of Stromal Cell-Derived Factor-1/Pre-B Cell Growth-Stimulating Factor Receptor, CXC Chemokine Receptor 4, on CD34+ Human Bone Marrow Cells is a Phenotypic Alteration for Committed Lymphoid Progenitors," The Journal of Immunology, vol. 163, 1999 (pp. 3612-3620).
Iwakura et al., "AMD-3100, a CXCR4 Antagonist, Augments Incorporation of Bone Marrow-Derived Eendothelial Progenitor

(56) References Cited

OTHER PUBLICATIONS

Cells into Sites of Myocardial Neovascularization," Abstract # 1127, Poster Board #—Session: 2931, Blood, vol. 100, No. 11, Nov. 16, 2002 (pp. 293A-294A).
Jackson et al., "Regeneration of ischemic cardiac muscle and vascular endothelium by adult stem cells," The Journal of Clinical Investigation, vol. 107, No. 1, Jun. 2011 (pp. 1395-1402).
Jennerex Biotherapeutics, "A Study of Recombinant Vaccinia Virus to Treat Malignant Melanoma," ClinicalTrials.gov: NCT00429312, First Posted: Jan. 31, 2007, Last Update: Jan. 15, 2015, https://clinicaltrials.gov/ct2/show/study/NCT00429312. Date Accessed, Mar. 25, 2019 (7 pages).
Jounce Therapeutics, Inc., "JTX-2011 Alone and in Combination With Anti-PD-1 or Anti-CTLA-4 in Subjects With Advanced and/or Refractory Solid Tumors (ICONIC)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).
Kawai et al., "Enhanced function with decreased internalization of carboxy-terminus truncated CXCR4 responsible for WHIM syndrome," Experimental Hematology, vol. 33, 2005 (pp. 460-468).
Kawai et al., "WHIM syndrome myelokathexis reproduced in the NOD/SCID mouse xenotransplant model engrafted with healthy human stem cells transduced with C-terminus-truncated CXCR4," Blood, vol. 109, No. 1, Jan. 1, 2007 (pp. 78-84), Epub Aug. 31, 2006.
Kawai et al., "WHIM syndrome: congenital immune deficiency disease," Current Opinion in Hematology, vol. 16, No. 1, Jan. 2009 (pp. 20-26).
Kim, et al., "CXCR4 signaling regulates metastasis of chemoresistant melanoma cells by a lymphatic metastatic niche," Cancer Research, vol. 70, No. 24, 2010 (pp. 10411-10421).
King, A. G. et al. "Rapid Mobilization of Murine Hematopoietic Stem Cells With Enhanced Engraftment Properties and Evaluation of Hematopoietic Progenitor Cell Mobilization in Rhesus Monkeys by a Single Injection of SB-251353, a Specific Truncated Form of the Human CXC Chemokine GROI3," Blood, vol. 97, No. 6, 2001 (pp. 1534-1542).
Kirkland et al., "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers," Blood, vol. 87, No. 9, 1996 (pp. 3963-3969).
Kocher et al. "Neovascularization of ischemic myocardium by human bone-marrow-derived angioblasts prevents cardiomyocyte apoptosis, reduces remodeling and improves cardiac function," Nature Medicine, vol. 7, 2001 (pp. 430-436).
Lagane et al., "CXCR4 dimerization and beta-arrestin-mediated signaling account for the enhanced chemotaxis to CXCL12 in WHIM syndrome," Blood, vol. 112, No. 1, Jul. 1, 2008 (pp. 34-44).
Lapidot et al., "Current understanding of stem cell mobilization: the roles of chemokines, proteolytic enzymes, adhesion molecules, cytokines, and stromal cells," Experimental Hematology, vol. 30, 2002, (pp. 973-981).
Lapidot et al., "The essential roles of the chemokine SDF-1 and its receptor CXCR4 in human stem cell homing and repopulation of transplanted immune-deficient NOD/SCID and NOD/SCID/B2m(null) mice," Leukemia, vol. 16, 2002 (pp. 1992-2003).
Lataillade et al., "Chemokine SDF-1 enhances circulating CD341 cell proliferation in synergy with cytokines: possible role in progenitor survival," Blood, vol. 95, No. 3., 1999 (pp. 756-768).
Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update: Jan. 17, 2018, https://clinicaltrials.gov/ct2/show/study/NCT02628574. Date Accessed, Mar. 18, 2019 (8 pages).
Leap Therapeutics, Inc., "Trial of TRX518 (Anti-GIIR mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).
Lee et al., "Coreceptor/Chemokine Receptor Expression on Human Hematopoietic Cells: Biological Implications for Human Immunodeficiency Virus-Type 1 Infection," Blood, vol. 93, No. 4, 1999 (pp. 1145-1156).
Liu et al., "Homozygous defect in HIV-1 coreceptor accounts for resistance of some multiply-exposed individuals to HIV-1 infection," Cell, vol. 86, No. 3, 1996 (pp. 367-377).
Lord, B. I. et al. "Mobilization of Early Hematopoietic Progenitor Cells with BB-1001-: A Genetically Engineered Variant of Human Macrophage Inflammatory Protein-1 alpha," Blood, vol. 85, No. 12, 1995 (pp. 3412-3415).
Ludwig Institute for Cancer Research, "A Phase ½ Study of Motolimod (VTX-2337) and MEDI473 6 in Subjects With Recurrent, Platinum-Resistant Ovarian Cancer for Whom Pegylated Liposomal Doxorubicin (PLD) is Indicated," ClinicalTrials.gov: NCT02431559, First Posted: May 1, 2015, Last Update: Aug. 7, 2018, https://clinicaltrials.gov/ct2/show/study/NCT02431559. Date Accessed, Mar. 25, 2019 (9 pages).
Ludwig Institute for Cancer Research, "A Phase ½ Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).
Lukacs et al., "AMD3100, a CxCR4 Antagonist, Attenuates Allergic Lung Inflammation and Airway Hyperreactivity," American Journal of Pathology, vol. 16, No. 4, 2002 (pp. 1353-1360).
Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).
M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).
M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).
M.D. Anderson Cancer Center, "Lirilumab With Rituximab for Relapsed, Refractory or High-risk Untreated Chronic Lymphocytic Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).
M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).
Ma et al., "The chemokine receptor CXCR4 is required for retention of B lineage and granulocytic precursors in the bone marrow microenvironment," Immunity, vol. 10, Apr. 1999 (pp. 463-471).
Maciejweski-Duval et al., "Altered chemotactic response to CXCL12 in patients carrying GATA2 mutations," Journal of Leukocyte Biology, vol. 99, No. 6. Epub Dec. 28, 2015 (pp. 1065-1076).
Maekawa et al., "Chemokine/Receptor Dynamics in the Regulation of Hematopoiesis," Internal Medicine, vol. 39, No. 2., 2000 (pp. 90-100).
Matthys et al.," AMD3100, a potent and specific antagonist of the stromal cell-derived factor-1 chemokine receptor CXCR4, inhibits autoimmune joint inflammation in IFN-gamma receptor-deficient mice," Journal of Immunology, vol. 167, No. 8, 2001 (p. 4686-4692).
Maximilian Diehn, "SABR-ATAC: A Trial of TGF-beta Inhibition and Stereotactic Ablative Radiotherapy for Early Stage Non-small

(56) References Cited

OTHER PUBLICATIONS

Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).

McCormick et al., "Impaired recruitment of Grk6 and beta-Arrestin 2 causes delayed internalization and desensitization of a WHIM syndrome-associated CXCR4 mutant receptor," PLoS One, vol. 4, 2009, (e8102).

McDermott et al., "A phase 1 clinical trial of long-term, low-dose treatment of WHIM syndrome with the CXCR4 antagonist plerixafor," Blood, vol. 123, No. 15, Apr. 10, 2014 (pp. 2308-2316).

McDermott et al., "The CXCR4 antagonist plerixafor corrects panleukopenia inpatients with WHIM syndrome," Blood, vol. 118, No. 18, Sep. 2, 2011 (pp. 4957-4962).

McDermott et al.,"Severe congenital neutropenia resulting from G6PC3 deficiency with increased neutrophil CXCR4 expression and myelokathexis," Blood Journal, vol. 116, 2010 (pp. 2793-2802).

McDermott, D. "Whim Syndrome," National Organization for Rare Disorders, 2013, 2016, https://rarediseases.org/rare-diseases/whim-syndrome. Date Accessed Sep. 27, 2018 (10 pages).

MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update: Jan. 29, 2018, https://clinicaltrials.gov/ct2/show/study/NCT02318394. Date Accessed, Mar. 18, 2019 (7 pages).

MedImmune LLC, "A Study in Adult Subjects With Select Advanced Solid Tumors," ClinicalTrials.gov: NCT02583165, First Posted: Oct. 22, 2015, Last Update: Jan. 8, 2019, https://clinicaltrials.gov/ct2/show/study/NCT02583165. Date Accessed, Mar. 18, 2019 (7 pages).

MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).

MedImmune LLC, "MEDI9447 Alone and in Combination With MEDI4736 in Adult Subjects With Select Advanced Solid Tumors," ClinicalTrials.gov: NCT02503774, First Posted: Jul. 21, 2015, Last Update: Mar. 11, 2019, https://clinicaltrials.gov/ct2/show/study/NCT02503774. Date Accessed, Mar. 18, 2019 (8 pages).

Merck KGaA, Darmstadt, Germany, "MSB0011359C (M7824) in Subjects With Metastatic or Locally Advanced Solid Tumors," ClinicalTrials.gov: NCT02699515, First Posted: Mar. 4, 2016, Last Update: Sep. 12, 2018, https://clinicaltrials.gov/ct2/show/study/NCT02699515. Date Accessed, Mar. 25, 2019 (8 pages).

Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted: Jan. 4, 2017, Last Update: Mar. 15, 2019, https://clinicaltrials.gov/ct2/show/study/NCT03010176. Date Accessed, Mar. 18, 2019 (11 pages).

Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).

Michael et al., "Exclusive and Persistent Use of the Entry Coreceptor CXCR4 by Human Immunodeficiency Virus Type 1 from a Subject Homozygous for CCR5 Δ32," Journal of Virology, vol. 72, No. 7, Jul. 1998 (pp. 6040-6047).

Miller, J. et al., "Novel N-substituted benzimidazole CXCR4 antagonists as potential anti-HIV agents," Bioorganic & Medicinal Chemistry Letters, vol. 20, 2010 (pp. 2125-2128).

Miller, J. et al., "Synthesis and SAR of novel isoquinoline CXCR4 antagonists with potent anti-HIV activity," vol. 20, 2010 (pp. 3026-3030).

Montane et al., "Prevention of murine autoimmune diabetes by CCL22-mediated Treg recruitment to pancreatic islets," Journal of Clinical Investigation, vol. 121, No. 8, Aug. 2011 (pp. 3024-3028).

Mosi R. M. et al., "The molecular pharmacology of AMD 11070: An orally bioavailable CXCR4 HIV entry inhibitor," Biochemical Pharmacology, vol. 83, 2012 (pp. 472-479).

Moskovits N. et al., "p53 attenuates cancer cell migration and invasion through repression of SDF-1/CXCL12 expression in stromal fibroblasts," Cancer Research, vol. 66, No. 22, Nov. 15, 2006 (pp. 10671-10676).

Motzer et al. (2015), "Nivolumab versus Everolimus in Advanced Renal-Cell Carcinoma," New England Journal of Medicine, vol. 373, No. 19, (pp. 1803-1813).

Moyle, et al., "Proof of Activity with AMD 11070, an Orally Bioavailable Inhibitor of CXCR4-Tropic HIV Type 1," Clinical Infectious Diseases, vol. 48, 2009 (pp. 798-805).

Murdoch et al., "Chemokine receptors and their role in inflammation and infectious diseases," Blood, vol. 95, 2000 (pp. 3032-3043).

Nagaraj S. et al., "Altered recognition of antigen is a mechanism of CD8+ T cell tolerance in cancer," Natural Medicine, vol. 13, No. 7, Jul. 2007 (pp. 828-835).

Nagase et al., "Expression of CXCR4 in Eosinophils: Functional Analyses and Cytokine-Mediated Regulation," The Journal of Immunology, vol. 164, No. 11, 2000 (pp. 5935-5943).

Nanki et al., "Cutting Edge: Stromal Cell-Derived Factor-1 is a Costimulator for CD4+ T Cell Activation," The Journal of Immunology, vol. 164, No. 10, 2000 (pp. 5010-5014).

Nash et al., "Allogeneic HSCT for autoimmune diseases: conventional conditioning regimens," Bone Marrow Transplantation, vol. 32, 2003 (pp. S77-S80).

National Cancer Institute (Nci), "A Phase I Study of Intravenous Recombinant Human IL-15 in Adults With Refractory Metastatic Malignant Melanoma and Metastatic Renal Cell Cancer," ClinicalTrials.gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).

National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).

National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials.gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).

National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).

National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).

National Cancer Institute (NCI), "Use of IL-15 After Chemotherapy and Lymphocyte Transfer in Metastatic Melanoma," ClinicalTrials.gov: NCT01369888, First Posted: Jun. 9, 2011, Last Update: Jan. 27, 2015, https://clinicaltrials.gov/ct2/show/study/NCT01369888. Date Accessed, Mar. 20, 2019 (9 pages).

National Cancer Institute, "Nivolumab and Ipilimumab in Treating Patients With HIV Associated Relapsed or Refractory Classical Hodgkin Lymphoma or Solid Tumors That are Metastatic or Cannot be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).

(56) References Cited

OTHER PUBLICATIONS

National Cancer Institute, "Nivolumab in Treating Patients With HTLV-Associated T-Cell Leukemia/Lymphoma," ClinicalTrials. gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).

Neumedicines Inc., "NM-IL-12 (rHuIL-12) in Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).

Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).

Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).

No author listed, SciFinder Search Results, No month listed, 2015 (39 pages).

No author listed, SciFinder Search Results, No month listed, 2015 (9 pages).

Novartis Pharmaceuticals, "A Phase I/Ib Study of NIZ985 in Combination WithPDR001 in Adults With Metastatic Cancers," ClinicalTrials.gov: NCT02452268, First Posted: May 22, 2015, Last Update: Oct. 2, 2018, https://clinicaltrials.gov/ct2/show/study/NCT02452268. Date Accessed, Mar. 20, 2019 (7 pages).

Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).

Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).

Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).

Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).

Novartis Pharmaceuticals, "Study of the Safety and Efficacy of MIW815 With PDR001 to Patients With Advanced/Metastatic Solid Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).

Nyunt, et al., "Pharmacokinetic Effect of AMD070, an Oral CXCR4 Antagonist, on CYP3 A4 and CYP2D6 Substrates Midazolam and Dextromethorphan in Healthy Volunteers," Journal of Acquired Immune Deficiency Syndrome, vol. 47, 2008 (pp. 559-565).

O'Hagen et al., "Apoptosis Induced by Infection of Primary Brain Cultures with Diverse Human Immunodeficiency Virus Type 1 Isolates: Evidence for a Role of the Envelope," Journal of Virology, vol. 73, No. 2, Feb. 1999 (pp. 897-906).

Okazaki, T. et al., "A rheostat for immune responses: the unique properties of PD1 and their advantages for clinical application," Nature Immunology, vol. 14, No. 12, Dec. 2013 (pp. 1212-1218).

Oncolytics Biotech, "A Study of REOLYSIN® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).

Oncolytics Biotech, "Efficacy Study of REOLYSIN® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).

Oncolytics Biotech, "Phase 2 Study of REOLYSIN® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).

OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).

Panka, DJ. et al., "HDM2 antagonism delays the development of sunitinib resistance inRCC xenografts: Effects of MI-319 on sunitinib-induced p53 activation, SDF-1 induction, and tumor infiltration by CD11b+/Gr-1+ myeloid suppressor cells," Molecular Cancer, vol. 12, No. 17, 2013 (pp. 1-12).

Peled et al., "The chemokine SDF-1 activates the integrins LFA-1, VLA-4, and VLA-5 on immature human CD34(+) cells: role in transendothelial/stromal migration and engraftment of NOD/SCID mice," Blood, vol. 95, No. 11, 2000 (pp. 3289-3296).

Pfizer, "A Study of Avelumab in Combination With Other Cancer Immunotherapies in Advanced Malignancies (JAVELIN Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).

Pfizer, "Avelumab in Combination Regimens That Include an Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update: Jan. 29, 2019, https://clinicaltrials.gov/ct2/show/study/NCT02951156. Date Accessed, Mar. 18, 2019 (11 pages).

Pike et al., "Nutrition: An Integrated Approach," Third Edition, John Wiley & Sons, 1984 (pp. 538-539).

Plexxikon, "A Combination Clinical Study of PLX3397 and Pembrolizumab to Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).

Ponath et al., "Chemokine receptor antagonists: novel therapeutics for inflammation and AIDS," Expert Opinion on Investigational Drugs, vol. 7, No. 1, 1998 (pp. 1-18).

Providence Health & Services," Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).

Providence Health & Services," Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).

Providence Health & Services," Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).

Providence Health & Services, "Stereotactic Body Radiation and Monoclonal Antibody to OX40 (MEDI6469) in Breast Cancer Patients With Metastatic Lesions (OX40 Breast)," ClinicalTrials. gov: NCT01862900, First Posted: May 27, 2013, Last Update: Mar.

(56) References Cited

OTHER PUBLICATIONS 6, 2019, https://clinicaltrials.gov/ct2/show/study/NCT01862900. Date Accessed, Mar. 18, 2019 (7 pages).
PsiOxus Therapeutics Ltd, "Phase I / Dose Expansion Study of Enadenotucirev in Ovarian Cancer Patients (OCTAVE)," ClinicalTrials.gov: NCT02028117, First Posted: Jan. 6, 2014, Last Update: Feb. 26, 2019, https://clinicaltrials.gov/ct2/show/study/NCT02028117. Date Accessed, Mar. 25, 2019 (8 pages).
PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd, First Posted: Dec. 21, 2015, Last Update: Mar. 4, 2019, https://clinicaltrials.gov/ct2/show/study/NCT02636036. Date Accessed, Mar. 25, 2019 (9 pages).
PubChem Open Chemistry Database, Compound Summary for CID 10890081, created Oct. 25, 2006 (14 pages).
PubChem Open Chemistry Database, Compound Summary for CID 12087079, created Feb. 7, 2007 (14 pages).
PubChem Open Chemistry Database, Compound Summary for CID 19046926, created Dec. 4, 2017 (11 pages).
PubChem Open Chemistry Database, Compound Summary for CID 70962830, created Mar. 21, 2013 (12 pages).
Rana et al., "Role of CCR5 in infection of primary macrophages and lymphocytes by macrophage-tropic strains of human immunodeficiency virus: resistance to patient-derived and prototype isolates resulting from the delta ccr5 mutation," Journal of Virology, vol. 71, No. 4, 1997 (pp. 3219-3227).
Ratajczak, et al., "The pleotropic effects of the SDF-1-CXCR4 axis in organogenesis, regeneration, andtumorigenesis," Leukemia, vol. 20, 2006 (pp. 1915-1924).
Reetz et al., "Highly Efficient Lipase-Catalyzed Kinetic Resolution of Chiral Amines" Chimia International Journal for Chemistry, vol. 48, No. 12, 1994 (p. 570).
Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update: Jan. 11, 2019, https://clinicaltrials.gov/ct2/show/study/NCT03002376. Date Accessed, Mar. 25, 2019 (6 pages).
Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).
Regeneron Pharmaceuticals, "Study of REGN 2810 Compared to Platinum-Based Chemotherapies in Participants With Metastatic NonSmall Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).
Regeneron Pharmaceuticals, "Study of REGN2810 and REGN1979 in Patients With Lymphoma," ClinicalTrials.gov: NCT02651662, First Posted: Jan. 11, 2016, Last Update: Sep. 11, 2018, https://clinicaltrials.gov/ct2/show/study/NCT02651662. Date Accessed, Mar. 25, 2019 (7 pages).
Regeneron Pharmaceuticals, "Study of REGN2810 in Patients With Advanced Cutaneous Squamous Cell Carcinoma," ClinicalTrials.gov: NCT02760498, First Posted: May 3, 2016, Last Update: Jan. 14, 2019, https://clinicaltrials.gov/ct2/show/study/NCT02760498. Date Accessed, Mar. 25, 2019 (6 pages).
Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).
Righi E. et al., "CXCL12/CXCR4 Blockade Induces Multimodal Antitumor Effects That Prolong Survival in an Immunocompetent Mouse Model of Ovarian Cancer," Cancer Research, vol. 71, No. 16, Aug. 15, 2011 (pp. 5522-5534).
Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).
Robert, et al., "Pembrolizumab versus Ipilimumab in Advanced Melanoma," New England Journal of Medicine, vol. 372, 2015 (pp. 2521-2532).
Salcedo et al., "Vascular endothelial growth factor and basic fibroblast growth factor induce expression of CXCR4 on human endothelial cells: In vivo neovascularization induced by stromal-derived factor-lalpha.Am," The American Journal of Pathology, vol. 154, No. 4, 1999 (pp. 1125-1135).
Saxena et al., "Efficacy and Mechanism of Action of CXCR4 Inhibition in B16 OVA Melanoma Model," The Society for Immunotherapy of Cancer Annual Meeting, National Harbor, Maryland, Nov. 8-12, 2017 (1 page).
Saxena et al., "Efficacy and Mechanism of Action of CXCR4 Inhibition in B16-OVA Melanoma Model," Journal for ImmunoTherapy of Cancer, Abstract, vol. 5, Suppl. 2, 2017 (p. 356).
Scala, et al., "Expression of CXCR4 predicts poor prognosis inpatients with malignant melanoma," Clinical Cancer Research, vol. 11, Mar. 1, 2005 (pp. 1835-1841).
Schlabach et al., "Cancer proliferation gene discovery through functional genomics," Science, vol. 319, No. 5863, Feb. 1, 2008 (pp. 620-624).
Schols et al., "Bicyclams, a class of potent anti-HIV agents, are targeted at the HIV coreceptor for Fusin/CXCR-4," Antiviral Research, vol. 35, 1997 (pp. 147-156).
Schols et al., "Inhibition of T-tropic HIV Strains by Selective Antagonization of the Chemokine Receptor CXCR4J," Journal of Experimental Medicine, vol. 186, No. 8, 1997 (pp. 1383-1388).
Schramm et al., "Cytopathicity of Human Immunodeficiency Virus Type 2 (HIV-2) in Human Lymphoid Tissue is Coreceptor Dependent and Comparable to That of HIV-1," Journal of Virology, vol. 74., No. 20, 2000 (pp. 184-192).
Schuitemaker et al., "Biological phenotype of human immunodeficiency virus type 1 clones at different stages of infection: progression of disease is associated with a shift from monocytotropic to T-cell-tropic virus population," Journal of Virology, vol. 66, No. 3, 1992 (pp. 1354-1360).
Sharma, P. et al., "Primary, Adaptive, and Acquired Resistance to Cancer Immunotherapy," Cell, vol. 168, No. 4, Feb. 9, 2017 (pp. 707-723).
Shen et al., "CXCR4-mediated STAT3 activation is essential for CXCL12-induced invasion in bladder cancer," Tumour Biology, vol. 34, 2013 (pp. 1839-1845).
Shojaei F. et al., "Tumor refractoriness to anti-VEGF treatment is mediated by CD11b+Gr1+ myeloid cells," Nature Biotechnology, vol. 25, No. 8, Aug. 2007 (pp. 911-920).
Sidney Kimmel Comprehensive Cancer Center at Johns Hopkins, "Anti-LAG-3 Alone & in Combination w/ Nivolumab Treating Patients w/Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).
Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).
SillaJen, Inc., "Hepatocellular Carcinoma Study Comparing Vaccinia Virus Based Immunotherapy Plus Sorafenib vs Sorafenib Alone (PHOCUS)," ClinicalTrials.gov: NCT02562755, First Posted: Sep. 29, 2015, Last Update: Feb. 6, 2019, https://clinicaltrials.gov/ct2/show/study/NCT02562755. Date Accessed, Mar. 25, 2019 (7 pages).
Silva et al., "Profiling essential genes in human mammary cells by multiplex RNA1 screening," Science, vol. 319, Feb. 1, 2008 (pp. 617-620).

(56) References Cited

OTHER PUBLICATIONS

Simmons et al., "CXCR4 as a Functional Coreceptor for Human Immunodeficiency Virus Type 1 Infection of Primary Macrophages," Journal of Virology, vol. 72, No. 10, 1998 (pp. 8453-8457).

Simmons et al., "Primary, syncytium-inducing human immunodeficiency virus type 1 isolates are dual-tropic and most can use either Lestr or CCR5 as coreceptors for virus entry," Journal of Virolology, vol. 70, No. 12, 1996 (pp. 8355-8360).

SK Chemicals Co., Ltd., "Study to Evaluate SID 530 Compared to Taxotere," ClinicalTrials.gov: NCT00931008, First Posted: Jul. 2, 2009, Last Update: Jan. 24, 2013, https://clinicaltrials.gov/ct2/show/study/NCT00931008. Date Accessed, Mar. 25, 2019 (6 pages).

Stone, et al., "Multiple-Dose Escalation Study of the Safety, Pharmacokinetics, and Biologic Activity of Oral AMD070, a Selective CXCR4 Receptor Inhibitor, in Human Subjects.," Antimicrobial Agents and Chemotherapy, vol. 51, No. 7, Jul. 2007 (pp. 2351-2358).

Supplementary European Search Report issued by the European Patent Office for European Patent App. No. 02775823.4, dated Dec. 23, 2004 (3 pages).

Supplementary European Search Report issued by the European Patent Office for European Patent App. No. 02805977.2, dated Apr. 16, 2008 (3 pages).

Supplementary European Search Report issued by the European Patent Office for European Patent App. No. 04752905.2, dated Mar. 12, 2010 (6 pages).

Supplementary European Search Report issued by the European Patent Office for European Patent App. No. 04814091.7, dated Mar. 10, 2008 (4 pages).

Supplementary European Search Report issued by the European Patent Office for European Patent App. No.04760161.2, dated Jun. 10, 2008 (3 pages).

Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar. 20, 2009, Last Update: Jul. 1, 2016, https://clinicaltrials.gov/ct2/show/study/NCT00866333. Date Accessed, Mar. 20, 2019 (6 pages).

Targovax Oy, "A Pilot Study of Sequential ONCOS-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials.gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).

Tarhini, et al., "Immune Monitoring of the Circulation and the Tumor Microenvironment in Patients with Regionally Advanced Melanoma Receiving Neoadjuvant Ipilimumab," PLoS One, vol. 9, No. 2, Feb. 2014 (p. e87705).

Teasdale et al., "Risk Assessment of Genotoxic Impurities in New Chemical Entities: Strategies to Demonstrate Control," Organic Process Research and Development, vol. 17, 2013 (p. 221-230).

Tersmette et al., "Differential Syncytium-Inducing Capacity of Human Immunodeficiency Virus Isolates: Frequent Detection of Syncytium-Inducing Isolates in Patients with Aquired Immune Deficiency Syndrome (AIDS) and AIDS-Related Complex," Journal of Virology, vol. 62, No. 6. (pp. 2026-2032).

Tesaro, Inc., "A Phase 1 Study of TSR-022, an Anti-UM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).

Therasse et al., "New Guidelines to Evaluate the Response to Treatment in Solid Tumors," Journal of the National Cancer Institute, vol. 92, No. 3, Feb. 2, 2000 (pp. 205-216).

Tortorici et al., "Influence of mild and moderate hepatic impairment on axitinib pharmacokinetics," Investigational New Drugs, vol. 29, 2011 (pp. 1370-1380).

Toyozawa, et al., "Chemokine receptor CXCR4 is a novel marker for the progression of cutaneous malignant melanoma," Japan Society of Histochemisty and Cytochemistry, vol. 45, No. 5, 2012 (pp. 293-299).

Trillium Therapeutics Inc., "A Trial of TTI-621 for Patients With Hematologic Malignancies and Selected Solid Tumors," ClinicalTrials.gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).

Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials.gov/ct2/show/study/NCT02890368. Date Accessed, Mar. 18, 2019 (9 pages).

Tu S.P. et al., "Curcumin induces the differentiation of myeloid-derived suppressor cells and inhibits their interaction with cancer cells and related tumor growth," Cancer Prevention Research, vol. 5, No. 2, Feb. 2012 (pp. 205-215).

Tumeh, et al., "PD-1 blockade induces responses by inhibiting adaptive immune resistance," Nature, vol. 515, No. 7528, Nov. 2014 (pp. 568-571).

U.S. Appl. No. 16/215,963, filed Dec. 11, 2018 (132 pages).
U.S. Appl. No. 16/311,020, filed Dec. 18, 2018 (237 pages).
U.S. Appl. No. 16/311,055, filed Dec. 18, 2018 (186 pages).
U.S. Appl. No. 16/311,083, filed Dec. 18, 2018 (276 pages).

University of Southern California," Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials.gov/ct2/show/study/NCT03092856. Date Accessed, Mar. 18, 2019 (11 pages).

University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).

Vanharanta et al., "Epigenetic expansion of VHL-HIF signal output drives multiorgan metastasis in renal cancer," Natural Medicine, vol. 19, No. 1., Jan. 2013 (pp. 50-56).

VentiRx Pharmaceuticals Inc., "A Phase Ib Study of Neoadjuvant of Cetuximab Plus Motolimod and Cetuximab Plus Motolimod Plus Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).

Ward et al., "Genetic and molecular diagnosis of severe congenital neutropenia," Current Opinion in Hematology, vol. 16, No. 1, Jan. 2009 (pp. 9-13).

Wong, "Comparison of the potential multiple binding modes of bicyclam, monocylam, and noncyclam small molecule CXC chemokine receptor 4 inhibitors," Molecular Pharmacology, vol. 74, No. 6, 2008 (pp. 1485-1495).

Zea A.H. et al. "Arginase-producing myeloid suppressor cells in renal cell carcinoma patients: a mechanism of tumor evasion," Cancer Research, vol. 65, No. 8, 2005 (pp. 3044-3048).

Zhang et al. "Preferential involvement of CXCR4 and CXCL12 in T cell migration toward melanoma cells," Cancer Biology & Therapy, vol. 5, No. 10, Oct. 2006 (pp. 1034-1312).

Zhang et al., "Chemokine Coreceptor Usage by Diverse Primary Isolates of Human Immunodeficiency Virus Type 1," Journal of Virology, vol. 72, No. 11, 1998 (pp. 9307-9312).

Zhang et al., "Will Multiple Coreceptors Need to be Targeted by Inhibitors of Human Immunodeficiency Virus Type 1 Entry?," Journal of Virology, vol. 73, No. 4., 1999 (pp. 3443-3448).

Zhao et al., "TNF signaling drives myeloid-derived suppressor cell accumulation," Journal of Clinical Investigation, vol. 122, No. 11, Nov. 2012 (pp. 4094-4104).

Zlotnik et al., "Chemokines: a new classification system and their role in immunity," Immunity, vol. 12, Feb. 2000 (pp. 121-127).

Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).

(56) References Cited

OTHER PUBLICATIONS

Zuelzer, "Myelokathexis'—A New Form of Chronic Granulocytopenia. Report of a case," New England Journal of Medicine, vol. 270, No. 14, 1964 (pp. 699-704).

Andtbacka et al., "X4P-001, an Orally Bioavailable CXCR4 Antagonist, Increases T Cell Infiltration in Human Metastatic Melanoma," The Society for Immunotherapy of Cancer Annual Meeting, National Harbor, Maryland, Nov. 8-12, 2017 (1 page).

Azilji et al., "New Developments in the Treatment of Metastatic Melanoma: Immune Checkpoint Inhibitors and Targeted Therapies," Anticancer Research, vol. 34, 2014 (pp. 1493-1506).

Boutsikou et al., "Tumour necrosis factor, interferon-gamma and interleukins as predictive markers of antiprogrammed Dell-death protein-1 treatment in advanced non-small cell lung cancer: a pragmatic approach in clinical practice," Therapeutic Advances in Medical Oncology, vol. 10, 2018 (pp. 1-8).

Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).

Courtney et al., "Optimizing recent advances in metastatic renal cell carincoma," Current Onocology Reports, vol. 11, No. 3, May 1, 2009 (pp. 218-226).

DePrimo et al., "Circulating protein biomarkers of pharmacodynamic activity of sunitinib in patients with metastatic renal cell carcinoma: modulation of VEGF and VEGF-related proteins," Journal of Translational Medicine, vol. 5, No. 32, Jul. 2, 2007 (11 pages).

Hamid et al., "Safety and Tumor Responses with Lambrolizumab (Anti-PD-1) in Melanoma," New England Journal of Medicine, vol. 369, No. 2, 2013 (pp. 134-144).

Neves, M. et al., Ligand-guided optimization of CXCR4 homology models for virtual screening using a multiple chemotype approach, Journal of Computer-Aided Molecular Design, vol. 24, No. 12, Oct. 20, 2010 (pp. 1023-1033).

O'Boyle et al., "Inhibition of CXCR4-CXCL12 chemotaxis in melanoma by AMD11070," British Journal of Cancer, vol. 108, No. 8, Apr. 2013 (pp. 1634-1640).

Parameswaran et al., "Combination of drug therapy in acute lymphblastic leukemia with CXCR4 antagonist," Leukemia, vol. 25, No. 8, Aug. 1, 2011 (pp. 1314-1323).

Reagen-Shaw et al., "Dose translation from animal to human studies revisited," The FASEB Journal, vol. 22, Mar. 2007 (pp. 659-661).

Rini et al., "Comparative effectiveness of axitinib versus soragenib in advanced renal cell carcinoma (AXIS): a Yandomised phase 3 trial," Lancet, vol. 378, 2011 (pp. 1931-1939).

Scala et al., "Molecular Pathways: Targeting the CXCR4-CXCL12 Axis-Untapped Potential in the Tumor Microenvironment," Clinical Cancer Research, vol. 21, No. 19, Jul. 21, 2015 (pp. 4278-4285).

Skerlj R. et al., "Discovery of Novel Small Molecule Orally Bioavailable C-X-C Chemokine Receptor 4 Antagonists That are Potent Inhibitors of T-Tropic (X4) HIV-1 Replication," Journal of Medicinal Chemistry, vol. 53, No. 8, 2010 (pp. 3376-3388).

Sullivan et al., "Pembrolizumab for Treatment of Patients with Advanced or Unresectable Melanoma," Clincal Cancer Research, vol. 12, No. 13, Apr. 30, 2015 (pp. 2892-2897).

FDA-approved AMD3100 (Mozobil@) drug label, New Drug Application (NDA): 022311, approval Action Date Dec. 15, 2008; downloaded Nov. 21, 2019 from accessdata.fda.gov.

*Novartis Pharms. Corp.* v. *West-Ward Pharms.* Int'l Ltd., 923 F.3d 1051 (Fed. Cir. 2019).

*OSI Pharmaceuticals LLC* v. *Apotex Inc.*, 939 F.3d 1375 (Fed. Cir. 2019); 2019 U.S. App. LEXIS 29851.

Choueiri, T. K., et al. (Oct. 19-23, 2018) Combination Therapy with the CXCR4 Inhibitor X4P-001 and Nivolumab Demonstrates Preliminary Anti-tumor Activity in RCC Patients that are Unresponsive to Nivolumab Alone, Poster session presented at the 2018 European Society for Medical Oncology (ESMO) Congress, Munich, Germany.

AnorMed, "X4P-001 Product Page," Adis Insight, Published Online: Mar. 20, 2019, http://adisinsight.springer.com/drugs/800017499. Date Accessed, Apr. 1, 2019 (5 pages).

Dudley et al., "CD8+ Enriched "Young" Tumor Infiltrating Lymphocytes Can Mediate Regression of Metastatic Melanoma," Clinical Cancer Research, vol. 16, No. 24, 2010 (pp. 6122-6131).

Gao et al., "Inlialumoral Balance of Regulatory and Cytotoxic T Cells is Associated With Prognosis of Hepatocellular Carcinoma After Resection," Journal of Clinical Oncology, vol. 25, No. 18, (pp. 2586-2593).

Gassenmeier et al., "CXC Chemokine Receptor 4 is Essential for Maintenance of Renal cell Carcinoma-Initiating Cells and Predicts Metastasis," Stem Cells Journals, vol. 31, No. 8, 2013 (pp. 1467-1476).

International Search Report and Written Opinion issued by the United States Patent and Trademark Office as International Searching Authority for International Patent Application No. PCT/US2017/026819, dated Jul. 21, 2017 (10 pages).

International Search Report and Written Opinion issued by the United States Patent and Trademark Office as International Searching Authority for International Patent Application No. PCT/US2017/038590, dated Oct. 17, 2017 (11 pages).

International Search Report and Written Opinion issued by the United States Patent and Trademark Office as International Searching Authority for International Patent Application No. PCT/US2017/038609, dated Oct. 31, 2017 (9 pages).

International Search Report and Written Opinion issued by the United States Patent and Trademark Office as International Searching Authority for International Patent Application No. PCT/US2017/038613, dated Dec. 28, 2017 (9 pages).

International Search Report and Written Opinion issued by the United States Patent and Trademark Office as International Searching Authority for International Patent Application No. PCT/US2019/049065, dated Nov. 15, 2019 (10 pages).

International Search Report and Written Opinion issued by the United States Patent and Trademark Office as International Searching Authority for International Patent Application No. PCT/US2018/038776, dated Nov. 20, 2018 (10 pages).

International Search Report and Written Opinion issued by the United States Patent and Trademark Office as International Searching Authority for International Patent Application No. PCT/US2018/059482, dated Jan. 17, 2019 (10 pages).

International Search Report and Written Opinion issued by the United States Patent and Trademark Office as International Searching Authority for International Patent Application No. PCT/US2019/027169, dated Jul. 3, 2019 (11 pages).

Langan et al., "Liver Directed Therapy for Renal Cell Carcinoma," Journal of Cancer, vol. 3, 2012 (pp. 184-190).

Motzer et al., "Nivolumab for Metastatic Renal Cell Carcinoma: Results of a Randomized Phase II Trial," Journal of Clinical Oncology, vol. 33, No. 13, 2015 (pp. 1430-1437).

PubChem Open Chemistry Database, Compound Summary for SID 219642471, created Oct. 21, 2014 (12 pages).

Raman et al., "Immunotherapy in Metastatic Renal Cell Carcinoma: A Comprehensive Review," Biomed Research International, vol. 2015, 2015 (pp. 1-9).

Andtbacka et al.,"X4P-001, and Orally Bioavailable CXCR4 Antagonist, Increases Immune Cell Infiltration and Tumor Inflammatory Status in the Microenvironment of Melanoma," The Society for Immunotherapy of Cancer Annual Meeting, Washington D.C., Nov. 7-11, 2018; Abstract (4 pages).

Burger et al., "CXCR4: a key receptor in the crosstalk between tumor cells and their microenvironment," Blood, 2006, 107(5): 1761-1767.

Choueir et al., "Combination Therapy with the CXCR4 Inhibitor X4P-001 and Nivolumab Demonstrates Preliminary Anti-tumor Activity in RCC Patients that are Unresponsive to Nivolumab Alone," 2018 ESMO Congress, Munich Germany, Oct. 19-23, 2018 (1 page).

Marco et al., "Ligand-guided optimization of CXCR4 homology models for virtual screening using a multiple chemotype approach," Journal of Computer-Aided Molecular Design, 2010, 24:1023-1033.

(56) References Cited

OTHER PUBLICATIONS

McDermott et al., "Safety and Efficacy of the Oral CXCR4 Inhibitor X4P-001 + Axitnib in Advanced Renal Cell Carcinoma Patients: An Analysis of Subgroup Responses by Prior Treatment," ESMO Congress, Barcelona, Spain, Sep. 30, 2019 (1 page).
McMahon, "VEGF Receptor Signaling in Tumor Angiogenesis," The Oncologist, 2000, 5(suppl 1):3-10.
Morimoto et al., "Enhancement of the CXCL12/CXCR4 axis due to acquisition of gemcitabine resistance in pancreatic cancer: effect of CXCR4 antagonists," BMC Cancer. 2016, 16(305):1-13.
Panka et al., 2016, "MDSC trafficking and function in RCC by CXCR4 in the presence of a VEGF-R antagonist is dependent on HIF-2? expression," European Journal of Cancer, 69(Supp 1): 146 (1 page).
Vaishampayan et al., 2018, "A Phase ½ Study Evaluating the Efficacy and Safety of the Oral CXCR4 Inhibitor X4P-001 in Combination with Axitinib in Patients with Advanced Renal Cell Carcinoma," 2018 American Society for Clinical Oncology Annual Meeting, Chicago, Illinois, Jun. 2, 2018 (1 page).
Zagzag et al., "Stromal Cell-Derived Factor-1 and CXCR4 Expression in Hemangioblastoma and Clear Cell-Renal Cell Carcinoma: von Hippel-Lindau Loss-of-Function Induces Expression of a Ligand and its Receptor," Cancer Research, 2005, 65(14): 6178-6188.
"Herr et al., ""Detection and quantification of blood-derived CD8+ T lymphocytes secreting tumor necrosis factor ? in response to HLA-A2.1-binding melanoma and viral peptide antigens""", Journal of Immunological Methods, 1996, vol. 191, No. 2, pp. 131-142".
"Herr et al., ""The use of computer-assisted video image analysis for the quantification of CD8+ T lymphocytes producing tumor necrosis factor ? spots in response to peptide antigens""", Journal of Immunological Methods, Apr. 25, 1997, vol. 203, Issue 2, pp. 141-152.".
"Patnaik et al., ""Phase I Study of Pembrolizumab (MK-3475; Anti-PD-1 Monoclonal Antibody) in Patients with Advanced Solid Tumors""", Clinical Cancer Research, Oct. 1, 2015, vol. 21, No. 19, pp. 4286-4293".
"Pembrolizumab," Drugbank, http://www.drugbank.ca/drugs/DB09037. Date Accessed, Jan. 18, 2016.
(Business Wire) X4 Pharmaceuticals Initiates Phase 1b Clinical Trial of Mavorixafor for the Treatment of Severe Congenital Neutropenia, Press release (online). Nov. 5, 2019 [retrieved on Oct. 25, 2021]. Retrieved from the Internet: [URL: https://www.bloomberg.com/press-releases/2019-11-05/x4-pharmaceuticals-initiates-phase-1b-clinical-trial-of-mavorixafor-for-the-treatment-of-severe-congenital-neutropenia].
Andreas Lundqvist et al., 31st Annual Meeting and Associated Programs of the Society for Immunotherapy of Cancer (SITC 2016): part one, Nov. 1, 2016, vol. 4, No. S1, XP055743746.
Anonymous: "Trial of X4P-001 in Patients With Advanced Renal Cell Carcinoma—Full Text View—ClinicalTrials.gov", Clinical Trials, Jan. 29, 2016, XP55786662, Retreived from the Internet: URL: https://clinicaltrials.gov/ct2/show/NCT02667886 (retreived on Mar. 17, 2021).
Assessment Report of the European Medicines Agency (EMA) for nivolumab EMEA, assessment report EMA/CHMP/76688/2015, Apr. 23, 2015.
Bai et al., "Novel anti-inflammatory agents targeting CXCR4: Design, synthesis, biological evaluation and preliminary pharmacokinetic study", Eur J. Med Chem. Aug. 2017, vol. 136 pp. 360-371.
Cao et al., "The Whim-like CXCRsomatic mutation activates AKT and ERK and promotes resistance to ibrutinib and other agents used in the treatment of Waldenstrom's Macroglobulinemia", Lukemia, Nature Publishing Group UK, Jun. 10, 2014, vol. 29, No. 1, pp. 169-176 XP036972305.
Curran et al., "PD-1 and CTLA-4 combination blockade expands infiltrating T cells and reduces regulatory T and myeloid cells within B16 melanoma tumors" PNAS, Mar. 2, 2010, vol. 107, No. 9, pp. 4275-4280.

Dale et al., Results of a phase 2 trial of an oral CXCR4 antagonist, mavorixafor, for treatment of WHIM syndrome. Blood. Dec. 24, 2020, Epub Aug. 31, 2020, vol. 136, No. 26, pp. 2994-3003.
Glassman et al., "Mechanistic considerations for the use of monoclonal antibodies for cancer therapy," Cancer Biology and Medicine, 2014, 11(1):20-33.
Gravina, G.L. et al., "The novel CXCR4 antagonist, PRX177561, reduces tumor cell proliferation andaccelerates cancer stem cell differentiation in glioblastoma preclinical models." Tumor Biology, 2017, 39(6):1-17.
Jacobson et al., "PET of Tumor CXCR4 Expression with 4-18F-T140", Nuclear Med., Nov. 2020, vol. 51, No. 11, pp. 1796-1804.
Jones et al., "CXCR chemokine receptor engagement modifies integrin dependent adhesion of renal carcinoma cells", Experimental Cell Research, 2007, vol. 313, p. 4051-4065.
Kashyap et al., "Ulocuplumab (BMS-936564 / MDX1338): a fully human anti-CXCR4 antibody induces cell death in chronic lymphocytic leukemia mediated through a reactive oxygen species-dependent pathway," Oncotarget, 2016, 7:2809-22.
Li, Z. et al., "Design, synthesis, and structure-activity-relationship of a novel series of CXCR4 antagonists," European Journal of Medicinal Chemistry, 2018, 149:30-44.
Magali Castells et al., "Implication of Tumor Microenviroment in Chemoresistance: Tumor-Associated Stromal Cells Protect Tumor Cells from Cell Death", International Journal of Molecular Sciences, Jul. 30, 2012, vol. 13, No. 8, pp. 9545-9571, XP055706477.
Malkov et al., "Multiplexed measurements of gene signatures in different analytes using the Nanostring nCounter™ Assay System", BMC Research Notes; 2009, vol. 2, No. 80 accessed Nov. 2, 2017, https:/bmcresnotes.biomedcentraLcom/articles/10.1186/1756-0500-2-80.
Mardiana et al., "A Multifunctional Role for Adjuvant Anti-4-1BB Therapy in Augmenting Antitumor Response by Chimeric Antigen Receptor T Cells" Cancer Res. Mar. 2017, vol. 77, No. 6, pp. 1296-1309.
Mukhta, E. et al., "Targeting microtubules by natural agents for cancer therapy," Molecular Cancer Therapeutics, 2014 13(2): 275-284.
Sato et al., "Intraepithelial CD8+ tumor-infiltrating lymphocytes and a high CD8+/regulatory T cell ratio are associated with favorable prognosis in ovarian cancer", PNAS, Dec. 20, 2005, vol. 102, No. 51, p. 18538-18543.
Sharma et al., "CD8 tumor-infiltrating lymphocytes are predictive of survival in muscle-invasive urothelial carcinoma", Proceedings of the National Academy of Sciences, Mar. 6, 2007, vol. 104, No. 10, pp. 3967-3972, XP055825486.
Shyamala et al., "Risk of tumor cell seeding through biopsy and aspiration cytology," Journal of International Society of Preventive and Community Dentistry, 2014, 4(1):5-11.
Spranger et al., (2013) "Up-Regulation of PD-L1, IDO, and Tregs in the Melanoma Tumor Microenvironment is Driven by CD8+ T Cells", Science Translational Medicine, vol. 5, No. 200, p. 200ra116.
Tamamura, H et al., "Identification of a CXCR4 antagonist, a T140 analog, as an anti-rheumatoid arthritis agent," FEBS Letters, 2004, 569: 99-104.
Ting-Chou et al., "Quantitative analysis of dose-effect relationships: the combined effects of multiple drugs or enzyme inhibitors", Adv Enzyme Regul, 1984, vol. 22, pp. 27-55.
Tunstall, "Quantifying Immune Cell Distribution in the Tumor Microenviroment Using HALO Spatial Analysis Tools", Application Note, Jul. 2016, Indica Labs, accessed Nov. 1, 2017, https://thepathologist.com/fileadmin/issues/AppNotes/0016-010-halo-app-note.pdf.
Waggott et al., "NanoStringNorm: an extensible R package for the pre-processing of NanoString mRNA and miRNA data", Bioinformatics, 2012, vol. 28, pp. 1546-1548.
Wang et al., "In Vitro Characterization of the Anti-PD-1 Antibody Nivolumab, BMS-936558, and In Vivo Toxicology in Non-Human Primates," Cancer Immunology Research, 2014, 2:1-11.
Yamazaki, N. et al. "Cytokine biomarkers to predict antitumor responses to nivolumab suggested in a phase 2 study for advanced melanoma," Cancer Science, 2017, 108(5): 1022-31.

(56) References Cited

OTHER PUBLICATIONS

Zhang, Y., et al. "Targeting primary acute myeloid leukemia with a new CXCR4 antagonist IgG1 antibody (PF-06747143)," Scientific Reports, 2017, 7: 7305 (2017).

* cited by examiner

METHODS FOR TREATING CANCER

CROSS-REFERENCE TO RELATED APPLICATIONS

This application claims the benefit of priority to U.S. Provisional Patent Application Ser. No. U.S. Ser. No. 62/319,857, filed Apr. 8, 2016, the entirety of which is hereby incorporated by reference.

FIELD OF THE INVENTION

The present invention relates to methods for treating cancer, for example, methods for treatment of patients with a cancer such as renal cell carcinoma.

BACKGROUND OF THE INVENTION

Renal cell carcinoma is the seventh most common cancer in men and the ninth most common cancer in women in the United States, with an estimated 65,000 new cases and 13,500 deaths expected in 2015. While stage I, II and III are frequently treated by partial or radical nephrectomy, up to 30% of patients with localized tumors experience relapse. Cytoreductive nephrectomy, followed by systemic therapy is generally recommended in patients with stage IV renal cell carcinoma with a surgically resectable primary tumor. Systemic therapy is then recommended for patients with residual metastatic disease. Chittoria and Rini (2013) Renal Cell Carcinoma; www.clevelandclinicmded.com/medical-pubs/diseasemanagement/nephrology/renal-cell-carcinoma/.

Adjuvant therapies with immunomodulating drugs, such as the anti-PD-1 antibody nivolumab (Opdivo®, Bristol-Myers Squibb, also known as ONO-4538, MDX1106 and BMS-936558), have shown potential to improve the overall survival in patients with RCC who had experienced disease progression during or after prior anti-angiogenic therapy.

The benefit of neoadjuvant chemo- and immunotherapy has been demonstrated in several operable cancers. Compared to adjuvant therapy, neoadjuvant therapy in patients with locally and regionally advanced cancer has several potential benefits:

Reducing the size of the primary and metastatic tumor increases the probability of achieving negative margin resection;

Tumor exposure to potentially effective systemic therapy is increased while blood and lymphatic vessels remain intact; and Collection of pre- and intra-operative samples of tumor tissue following neoadjuvant therapy offers real-time, in vivo assessment of the effects of the therapy on the tumor cells, the tumor microenvironment (TME), and the immune system.

DETAILED DESCRIPTION OF CERTAIN EMBODIMENTS OF THE INVENTION

CXCR4 (C—X—C chemokine receptor type 4) is a chemokine receptor expressed on a wide range of cell types, including normal stem cells, hematopoietic stem cells (HSC), mature lymphocytes, and fibroblasts. CXCL12 (previously referred to as SDF-1α) is the sole ligand for CXCR4. The primary physiologic functions of the CXCL12/CXCR4 axis include the migration of stem cells both during embryonic development (CXCR4−/− knock-out embryos die in utero) and subsequently in response to injury and inflammation. Increasing evidence indicates multiple potential roles for CXCR4/CXCL12 in malignancy. Direct expression of one or both factors has been observed in several tumor types. CXCL12 is expressed by cancer-associated fibroblasts (CAFs) and is often present at high levels in the TME. In clinical studies of a wide range of tumor types, including breast, ovarian, renal, lung, and melanoma, expression of CXCR4/CXCL12 has been associated with a poor prognosis and with an increased risk of metastasis to lymph nodes, lung, liver and brain, which are sites of CXCL12 expression. CXCR4 is frequently expressed on melanoma cells, particularly the CD133+ population that is considered to represent melanoma stem cells and in vitro experiments and murine models have demonstrated that CXCL12 is chemotactic for those cells.

Nivolumab (Opdivo®, Bristol-Myers Squibb, also known previously as ONO-4538, MDX1106 and BMS-936558) is a human IgG4 anti-PD-1 monoclonal antibody. It belongs to the emerging class of immunotherapeutics referred to as checkpoint modulators (CPM). These agents have been developed based on observations that in multiple types of malignancies, the tumor suppresses the host anti-tumor immune response by exploiting counter-regulatory mechanism that normally act as "checkpoints" to prevent the overactivation of the immune system in infection and other situations. In the case of melanoma, PD-L1 is expressed by cells in the TME, engages PD-1, a membrane-associated receptor on CD8+ effector T cells, and triggers inhibitory signaling that reduces the killing capacity of cytotoxic T cells.

Nivolumab is currently FDA approved for the treatment of patients with advanced renal cell carcinoma (RCC), who have received prior anti-angiogenic therapy. The recommended dose of nivolumab is 3 mg/kg administered as an intravenous infusion over 60 minutes every 2 weeks until disease progression or unacceptable toxicity. In a clinical trial, patients previously treated with nivolumab showed improved overall survival compared with patients being treated with a cancer chemotherapeutic, everolimus.

Multiple observations implicate the CXCL12/CXCR4 axis in contributing to the lack (or loss) of tumor responsiveness to angiogenesis inhibitors (also referred to as "angiogenic escape"). In animal cancer models, interference with CXCR4 function has been demonstrated to disrupt the tumor microenvironment (TME) and unmask the tumor to immune attack by multiple mechanisms, including eliminating tumor re-vascularization and increasing the ratio of CD8+ T cells to Treg cells. These effects result in significantly decreased tumor burden and increased overall survival in xenograft, syngeneic, as well as transgenic, cancer models. See Vanharanta et al. (2013) Nat Med 19: 50-56; Gale and McColl (1999) BioEssays 21: 17-28; Highfill et al. (2014) Sci Transl Med 6: ra67; Facciabene et al. (2011) Nature 475: 226-230.

X4P-001, formerly designated AMD11070, is a potent, orally bioavailable CXCR4 antagonist (see Montane et al. (2011) J Clin Invest 121: 3024-8), that has demonstrated activity in solid and liquid tumor models (see Acharyya et al. (2012) Cell 150: 165-78, and unpublished data) and has previously (under the designations AMD070 and AMD11070) been in Phase 1 and 2a trials involving a total of 71 healthy volunteers (see Montane et al. (2011) J Clin Invest 121: 3024-8; Zhao et al. (2012) J Clin Invest 122: 4094-4104; Silva et al. (2008) Science 319: 617-20) and HIV-infected subjects (see Schlabach et al. (2008) Science 319: 620-24; Shen et al. (2013) Tumour Biol 34: 1839-45). These studies demonstrated that oral administration of up to 400 mg BID for 3.5 days (healthy volunteers) and 200 mg BID for 8-10 days (healthy volunteers and HIV patients) was well-tolerated with no pattern of adverse events or clinically significant laboratory changes. These studies also demonstrated pharmacodynamic activity, with dose- and concentration-related changes in circulating white blood cells (WBCs); and a high volume of distribution (VL), suggesting high tissue penetration.

Plerixafor (formerly designated AMD3100, now marketed as Mozobil) is the only CXCR4 antagonist currently FDA approved. Plerixafor is administered by subcutaneous injection and has a very short half life; the only FDA-approved indication is for courses of 3 to 5 days to release HSC from the bone marrow into the peripheral blood for harvesting. Both X4P-001 and plerixafor have been studied in murine models of melanoma, renal cell carcinoma, and ovarian cancer and have demonstrated significant anti-tumor activity, including decreased metastasis and increased overall survival. The treatment effect has been associated with decreased presence of myeloid-derived suppressor cells (MDSCs) in the TME and increased presence of tumor-specific CD-8+ effector cells. See D'Alterio, et al. (2012) Cancer Immunol Immunother 61:1713-1720; Feig, et al. (2013) PNAS 110:20212-20217; and Zhang et al. (2006) Cancer Biol Ther. 5:1034-1312.

Without wishing to be bound by any particular theory, it is believed that administration of X4P-001 will increase the density of CD8+ T cells among tumor cells and that this effect will be sustained or increased when X4P-001 is given in combination with nivolumab. Because X4P-001 is well-tolerated in the body, and may increase the ability of the body to mount a robust anti-tumor immune response, administering X4P-001 in combination with checkpoint modulators may substantially increase the objective response rate in multiple tumor types, the frequency of durable long-term responses, and overall survival.

It is further believed that such results will be achieved with comparatively little toxicity because CXCR4-targeted drugs are not be expected to induce cell cycle arrest in bone marrow and other normal proliferating cell populations. Accordingly, the present invention provides significant advantages in treatment outcomes utilizing the low toxicity and effects of the CXCR4 inhibitor AMD11070 (X4P-001) on MDSC trafficking, differentiation and tumor cell gene expression in RCC.

It has now been found that CXCR4 antagonism by X4P-001 provides significant effects which in turn would provide significant treatment benefits in patients with advanced renal cell carcinoma and other cancers by multiple mechanisms. In certain embodiments, administration of X4P-001 increases the density of CD8+ T cells, thereby resulting in increased anti-tumor immune attack. In certain embodiments, administration of X4P-001 additionally decreases neoangiogenesis and tumor vascular supply. In other embodiments, administration of X4P-001 interferes with the autocrine effect of increased expression by tumors of both CXCR4 and its only ligand, CXCL12, thereby reducing cancer cell metastasis.

In one aspect of the present invention, patients with advanced forms of cancer, including kidney cancer, such as renal cell carcinoma, are treated with X4P-001, either as a single agent (monotherapy), or in combination with an immune checkpoint inhibitor, such as nivolumab. Nivolumab is an antibody to PD-1, which binds to the programmed cell death 1 receptor (PD-1) to prevent the receptor from binding to the inhibitory ligand PDL-1, thus overriding the ability of tumors to suppress the host anti-tumor immune response, dubbed an immune checkpoint inhibitor.

Without wishing to be bound by any particular theory, it is believed that by combining the two medicaments X4P-001, or a pharmaceutically acceptable salt thereof, and an immune checkpoint inhibitor, a patient's treatment outcome can be further improved by increasing the body's ability to mount a robust anti-tumor immune response.

In some embodiments, X4P-001, or a pharmaceutically acceptable salt thereof, is administered to a patient in a fasted state.

In some embodiments, the present invention provides a method for treating patients with cancer that presents as a solid tumor, particularly renal cell carcinoma. In some embodiments, the patient has resectable RCC, meaning that the patient's tumor is deemed susceptible to being removed by surgery. In other embodiments, the patient has unresectable carcinoma, meaning that the patient's tumor has been deemed not susceptible to being removed by surgery.

In some embodiments, the present invention provides a method for treating advanced cancer, such as kidney cancer or renal cell carcinoma, in a patient in need thereof comprising administering X4P-001, or a pharmaceutically acceptable salt or pharmaceutical composition thereof. In certain embodiments, the patient was previously administered an immune checkpoint inhibitor. In some embodiments, the patient was previously administered an immune checkpoint inhibitor selected from the group consisting of nivolumab (Opdivo®, Bristol-Myers Squibb), pembrolizumab (Keytruda®, Merck) and ipilimumab (Yervoy®, Bristol-Myers Squibb). In some embodiments, the patient has previously received a tumor resection or anticancer chemotherapy or immunotherapy, such as previous treatment with anti-angiogenic therapy and/or an immune checkpoint inhibitor but not X4P-001 or a pharmaceutically acceptable salt thereof.

In certain embodiments, the present invention provides a method for treating cancer in a patient comprising administering to said patient X4P-001 or a pharmaceutically acceptable salt thereof in combination with an immunotherapeutic drug, such as an immune checkpoint inhibitor. In certain embodiments, the X4P-001 and the checkpoint inhibitor are administered simultaneously or sequentially. In certain embodiments, X4P-001 or a pharmaceutically acceptable salt thereof is administered prior to the initial dosing with the immune checkpoint inhibitor. In certain embodiments, the immune checkpoint inhibitor is administered prior to the initial dosing with X4P-001 or a pharmaceutically acceptable salt thereof.

In certain embodiments, the immune checkpoint inhibitor is selected from a PD-1 antagonist, a PD-L1 antagonist, and a CTLA-4 antagonist. In some embodiments, X4P-001 or a pharmaceutically acceptable salt thereof is administered in combination with an immunotherapeutic drug selected from the group consisting of nivolumab (Opdivo®, Bristol-Myers Squibb), ipilimumab (Yervoy®, Bristol-Myers Squibb); and pembrolizumab (Keytruda®, Merck). In some embodiments, X4P-001 or a pharmaceutically acceptable salt thereof is administered in combination with nivolumab (Opdivo®, Bristol-Myers Squibb) previously known as BMS-93568, MDX1106 or ONO-4538.

Other immune checkpoint inhibitors in development are suitable for use in combination with X4P-001 or a pharmaceutically acceptable salt thereof. These include atezolizumab (Genentech/Roche), also known as MPDL3280A, a fully humanized engineered antibody of IgG1 isotype against PD-L1, in clinical trials for non-small cell lung cancer and advanced bladder cancer such as advanced urothelial carcinoma; and as adjuvant therapy to prevent cancer from returning after surgery; durvalumab (AstraZeneca), also known as MEDI4736, in clinical trials for metastatic breast cancer, multiple myeloma, esophageal cancer, myelodysplastic syndrome, small cell lung cancer, head and neck cancer, renal cancer, glioblastoma, lymphoma and solid malignancies; pidilizumab (CureTech), also known as CT-011, an antibody that binds to PD-1, in clinical trials for diffuse large B-cell lymphoma and multiple myeloma; avelumab (Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors.

Nivolumab (Opdivo®, BMS-93568/MDX1106; Bristol-Myers Squibb), is a fully human IgG4 monoclonal antibody that acts as an immunomodulator by binding to the programmed cell death 1 (PD-1) receptor and selectively blocking interaction with its ligands PD-L1 and PD-L2. The structure and other properties of nivolumab are specified at http://www.drugbank.ca/drugs/DB09035, accessed on Mar. 14, 2016, the disclosure of which is hereby incorporated herein. Nivolumab is approved for use in treatment of patients with advanced renal cell carcinoma who have received prior anti-angiogenic therapy; as a single agent in certain types of unresectable or metastatic melanoma; in treating unresectable or metastatic melanoma or in combination with ipilimumab in treating unresectable or metastatic melanoma; and for treatment of metastatic non-small cell lung cancer and progression on or after platinum-based chemotherapy. Additionally, nivolumab has been tested or mentioned as a possible treatment in other oncologic indications, including solid tumors; skin melanoma; glioblastoma; glioma; gliosarcoma; astrocytoma; brain cancer; leukemia; acute myeloid leukemia; chronic myeloid leukemia; chronic lymphocytic leukemia; advanced liver cancer or hepatocellular carcinoma; uveal melanoma; prostate cancer; pancreatic neoplasm and pancreatic cancer; bladder cancer; colorectal cancer; myelodysplastic syndrome; Hodgkin Lymphoma; Non-Hodgkin Lymphoma; multiple myeloma; cervical cancer; endometrial cancer; uterine cancer; ovarian cancer and ovarian carcinoma; peritoneal carcinoma; head and neck squamous cell cancer; gastric cancer; esophageal cancer; Kaposi sarcoma; breast neoplasm, breast adenocarcinoma and breast cancer; bone sarcoma; soft tissue sarcoma; meningiomas; and mesothelioma.

In a phase 3 trial of over 800 patients with advanced clear-cell renal-cell carcinoma, for which they had received previous treatment with one or two regimens of antiogenic therapy were randomly assigned to receive 3 mg/kg body weight of nivolumab, intravenously every two weeks, or a 10 mg everolimus tablet orally daily. Patients treated with nivolumab exhibited longer median overall survival, decreased hazard ratio for death, and higher objective response rate than those patients treated with nivolumab (25%) compared to everolimus (5%) ($P<0.001$), with lower incidence of Grade 3 or 4 treatment-related adverse events (Motzer et al. (2015), New England Journal of Medicine, 373:1803-1813).

In its current prescribed labeling for unresectable or metastatic renal cell carcinoma, the recommended course of administration for nivolumab is 3 mg/kg as an intravenous infusion over 60 minutes every two weeks, until disease progression or unacceptable toxicity. In the discretion of the clinician, depending upon individual tolerance, the prescribed dose of nivolumab may be increased, for example, increased in dosage and/or frequency. In the discretion of the clinician, together with the warnings provided with prescribing information, administration of nivolumab may be discontinued, or the dose reduced in the case of significant adverse effects.

In some embodiments, the present invention provides a method for treating renal cell carcinoma in a patient by administering X4P-001 or a pharmaceutically acceptable salt thereof in combination with an immune checkpoint inhibitor. In some embodiments, the carcinoma is resectable and metastatic. In other embodiments, the carcinoma is unresectable and metastatic. In some embodiments, the immune checkpoint inhibitor is nivolumab.

In some embodiments, the present invention provides a method for treating a refractory cancer in a patient, wherein said method comprises administering to said patient X4P-001 or a pharmaceutically acceptable salt thereof in combination with an immune checkpoint inhibitor. In some embodiments, the refractory cancer is metastatic renal cell carcinoma whose tumors express PD-L1, and who have disease progression after treatment with anti-angiogenic therepy or platinum-containing chemotherapy. In some embodiments, the refractory cancer is metastatic renal cell carcinoma and the immune checkpoint inhibitor is nivolumab.

In some embodiments of the disclosed methods, X4P-001, or a pharmaceutically acceptable salt thereof, is administered to a patient in need thereof in a fasted state and the immune checkpoint inhibitor is administered to the patient in either a fasted or fed state.

In certain embodiments, the present invention provides a method for treating cancer in a patient, wherein said method comprises administering to said patient X4P-001 or a pharmaceutically acceptable salt thereof in combination with an immune checkpoint inhibitor, further comprising the step of obtaining a biological sample from the patient and measuring the amount of a disease-related biomarker. In some embodiments, the biological sample is a blood sample. In certain embodiments, the disease-related biomarker is circulating CD8+ cells, plasma levels of PD-1, and/or plasma levels of PDL-1.

In certain embodiments, the present invention provides a method for treating advanced cancer, such as metastatic renal cell carcinoma, in a patient in need thereof, wherein said method comprises administering to said patient X4P-001 or a pharmaceutically acceptable salt thereof in combination with nivolumab, further comprising the step of obtaining a biological sample from the patient and measuring the amount of a disease-related biomarker. In some embodiments, the biological sample is a blood sample. In certain embodiments, the disease-related biomarker is circulating CD8+ cells, plasma levels of PD-1, and/or plasma levels of PDL-1.

In other embodiments of the invention, X4P-001 or a pharmaceutically acceptable salt thereof is administered in combination with an immune checkpoint inhibitor. The immune checkpoint inhibitor may be an antibody to PD-1, PDL-1, or CTLA-4. In certain embodiments, the immune checkpoint inhibitor is selected from the group consisting of nivolumab, pembrolizumab, and ipilimumab.

In some embodiments, the present invention provides a method of treating cancer in a patient, wherein said method comprises administering to said patient X4P-001 or a pharmaceutically acceptable salt thereof in combination with an immune checkpoint inhibitor, wherein the X4P-001 and the immune checkpoint inhibitor act synergistically. One of ordinary skill in the art will appreciate that active agents (such as X4P-001 and an immune checkpoint inhibitor) act synergistically when the combination of active agents results in an effect that is greater than the additive effect of each agent taken separately. In some embodiments, the immune checkpoint inhibitor is nivolumab.

Dosage and Formulations

X4P-001 is a CXCR4 antagonist, with molecular formula $C_{21}H_{27}N_5$; molecular weight 349.48 amu; and appearance as a white to pale yellow solid. Solubility: X4P-001 is freely soluble in the pH range 3.0 to 8.0 (>100 mg/mL), sparingly soluble at pH 9.0 (10.7 mg/mL) and slightly soluble at pH 10.0 (2.0 mg/mL). X4P-001 is only slightly soluble in water. Melting point: 108.9° C.

The chemical structure of X4P-001 is depicted below.

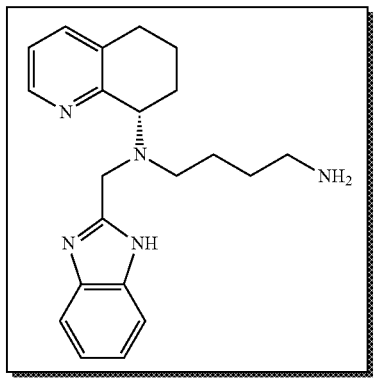

X4P-001

In certain embodiments, a pharmaceutical composition containing X4P-001 or a pharmaceutically acceptable salt thereof is administered orally in an amount from about 200 mg to about 1200 mg daily. In certain embodiments, the dosage composition may be provided twice a day in divided dosage, approximately 12 hours apart. In other embodiments, the dosage composition may be provided once daily. The terminal half-life of X4P-001 has been generally determined to be between about 12 to about 24 hours, or approximately 14.5 hrs. Dosage for oral administration may be from about 100 mg to about 1200 mg once or twice per day. In certain embodiments, the dosage of X4P-001 or a pharmaceutically acceptable salt thereof useful in the invention is from about 200 mg to about 600 mg daily. In other embodiments, the dosage of X4P-001 or a pharmaceutically acceptable salt thereof useful in the invention may range from about 400 mg to about 800 mg, from about 600 mg to about 1000 mg or from about 800 mg to about 1200 mg daily. In certain embodiments, the invention comprises administration of an amount of X4P-001 or a pharmaceutically acceptable salt thereof of about 10 mg, about 20 mg, about 25 mg, about 50 mg, about 75 mg, about 100 mg, about 125 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, or about 1600 mg.

In some embodiments, a provided method comprises administering to the patient a pharmaceutically acceptable composition comprising X4P-001 or a pharmaceutically acceptable salt thereof wherein the composition is formulated for oral administration. In certain embodiments, the composition is formulated for oral administration in the form of a tablet or a capsule. In some embodiments, the composition comprising X4P-001 or a pharmaceutically acceptable salt thereof is formulated for oral administration in the form of a capsule.

In certain embodiments, a provided method comprises administering to the patient one or more capsules comprising 100-1200 mg X4P-001 or a pharmaceutically acceptable salt thereof as an active ingredient; and one or more pharmaceutically acceptable excipients. In some embodiments, each capsule or capsules administered may independently comprise about 25 mg, about 50 mg, about 75 mg, about 100 mg, about 150 mg, about 200 mg, about 400 mg or about 800 mg X4P-001 or a pharmaceutically acceptable salt thereof as an active ingredient; and one or more pharmaceutically acceptable excipients.

In certain embodiments, the present invention provides a pharmaceutical composition comprising X4P-001 or a pharmaceutically acceptable salt thereof, one or more diluents, a disintegrant, a lubricant, a flow aid, and a wetting agent. In some embodiments, the present invention provides a composition comprising 10-1200 mg X4P-001 or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In some embodiments, the present invention provides a unit dosage form wherein said unit dosage form comprises a composition comprising 10-200 mg X4P-001, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In certain embodiments, the present invention provides a unit dosage form comprising a composition comprising X4P-001 or a pharmaceutically acceptable salt thereof, present in an amount of about 10 mg, about 20 mg, about 25 mg, about 50 mg, about 75 mg, about 100 mg, about 125 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, or about 1600 mg. In some embodiments, a provided composition (or unit dosage form) is administered to the patient once per day, twice per day, three times per day, or four times per day. In some embodiments, a provided composition (or unit dosage form) is administered to the patient once per day or twice per day. In some embodiments, the unit dosage form comprises a capsule containing about 25 mg, about 50 mg, about 75 mg, about 100 mg, about 150 mg, about 200 mg, about 400 mg, or about 800 mg of X4P-001, or a pharmaceutically acceptable salt thereof.

In some embodiments, the present invention provides a unit dosage form comprising a pharmaceutical composition comprising:
(a) X4P-001, or a pharmaceutically acceptable salt thereof—about 30-40% by weight of the composition;
(b) microcrystalline cellulose—about 20-25% by weight of the composition;
(c) dibasic calcium phosphate dehydrate—about 30-35% by weight of the composition;

(d) croscarmellose sodium—about 5-10% by weight of the composition;
(e) sodium stearyl fumarate—about 0.5-2% by weight of the composition;
(f) colloidal silicon dioxide—about 0.1-1.0% by weight of the composition; and
(g) sodium lauryl sulfate—about 0.1-1.0% by weight of the composition.

In some embodiments, the present invention provides a unit dosage form comprising a composition comprising:
(a) X4P-001, or a pharmaceutically acceptable salt thereof—about 37% by weight of the composition;
(b) microcrystalline cellulose—about 23% by weight of the composition;
(c) dibasic calcium phosphate dehydrate—about 32% by weight of the composition;
(d) croscarmellose sodium—about 6% by weight of the composition;
(e) sodium stearyl fumarate—about 1% by weight of the composition;
(f) colloidal silicon dioxide—about 0.3% by weight of the composition; and
(g) sodium lauryl sulfate—about 0.5% by weight of the composition.

In some embodiments, the present invention provides a unit dosage form comprising a composition comprising:
(a) X4P-001, or a pharmaceutically acceptable salt thereof—about 55-65% by weight of the composition;
(b) microcrystalline cellulose—about 10-15% by weight of the composition;
(c) dibasic calcium phosphate dehydrate—about 15-20% by weight of the composition;
(d) croscarmellose sodium—about 5-10% by weight of the composition;
(e) sodium stearyl fumarate—about 0.5-2% by weight of the composition;
(f) colloidal silicon dioxide—about 0.1-1.0% by weight of the composition; and
(g) sodium lauryl sulfate—about 0.1-1.0% by weight of the composition.

Nivolumab has been approved by the FDA for treatment of unresectable or metastatic renal cell carcinoma and is generally administered at a dosage of 3 mg/kg as an intravenous infusion over 60 minutes once every 2 weeks. Generally, the amount of nivolumab or other immune checkpoint inhibitor useful in the present invention will be dependent upon the size, weight, age and condition of the patient being treated, the severity of the disorder or condition, and the discretion of the prescribing physician.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

The contents of each document cited in the specification are herein incorporated by reference in their entireties.

EXEMPLIFICATION

Example 1—Measurement of CD8+ T Cells

Assessment of the effectiveness of the present invention can be made in part by measurement of the CD8+ T cell population. Expanding or increasing the density of CD8+ T cells, such as T-infiltrating lymphocytes (TIL), can help increase tumor recognition and ultimately tumor regression. Dudley et al., (2010) Clin. Cancer Research, 16:6122-6131. CD8+ T cells can be detected, isolated and quantified utilizing methods described in Herr et al., (1996), J. Immunol. Methods 191:131-142; Herr et al., (1997) J. Immunol. Methods 203:141-152; and Scheibenbogen et al., (2000) J Immunol. Methods 244:81-89. The full disclosure of each of these publications is hereby incorporated by reference herein.

Example 2—Renal Cell Carcinoma Xenograft Model

In order to assess the effects of the present invention on the presence of human CD8+ effector T cells, accumulation of Treg cells in the tumor microenvironment and, ultimately, the effects on renal cell carcinoma, a human RCC xenograft model can be used, as described in Pavia-Jimenez et al. (2014) Nature Protocols 9:1848-1859; Grisanzio et al. (2011) J Pathol 225:212-221. The full disclosure of each of these publications is hereby incorporated by reference herein.

Example 3—Criteria for Evaluating Response in Patients with Solid Tumors

The response of patients with solid tumors to treatment can be evaluated using the criteria set forth in RECIST 1.1, Eisenhauer et al., (2009) Eur. J. Cancer, 45:228-247, the full disclosure of which is hereby incorporated by reference herein.

Example 4—Cytokine and Chemokine Studies

The in vivo effects of treatment with X4P-001 and nivolumab on chemokine production by RCC cells are assessed as follows:

Tumors excised from the mice undergoing treatment with X4P-001 and nivolumab in Example 1 and 2 are analyzed by RT-PCR for drug-induced changes in the expression of M-CSF (CSF-1), CXCL1 (MGSA/gro-), CXCL2 (MIP-2/gro-), MIP-2/gro-, CXCL5 (ENA-78), CXCL6 (GCP-2), CXCL8 (IL-8), GM-CSF, VEGF, TNF, CCL22, and CCL28. The various ELR-containing CXCL chemokines listed are known to activate CXCR2 (Gale and McColl (1999) BioEssays 21: 17-28), a chemokine receptor recently implicated in MDSC recruitment (Highfill et al. (2014) Sci Transl Med 6: ra67). The cytokines VEGF, GM-CSF, and TNF are also thought to mediate MDSC chemotaxis into tumor tissue. CCL22 and CCL28 have been likewise implicated in the recruitment of Treg cells (Facciabene et al. (2011), Nature 475: 226-230; Montane et al. (2011) J Clin Invest 2011; 121: 3024-8).

Numerous chemokines and other inflammatory mediators have been shown to regulate the trafficking of MDSC into tumor tissue (Highfill et al. (2014) Sci Transl Med 6: ra67; Acharyya et al. (2012) Cell 150:165-7813; Zhao et al. (2012) Clin Invest 122: 4094-4104). To determine which chemokines/cytokines are responsible for the influx of MDSC into RCC during treatment with VEGF-targeted therapies, CD11b+/Gr-1+ MDSC are isolated from the spleens of tumor-bearing mice undergoing treatment with nivolumab. The MDSC are then infected with a small pooled lentiviral shRNA library (DeCode GIPZ, Thermo Scientific) for a select group of G protein-coupled and other receptors known to regulate MDSC trafficking. The library will include shRNAs for TNFR-1 and -2, IL-4R, and whole array of CXCR and CCR chemokine receptors (CXCR1-5, CCR 1-9). Several of these (e.g. CXCR-1, -2, and -4) engage chemokines known to promote MDSC recruitment (Highfill et al. (2014) Sci Transl Med 6: ra67; Acharyya et al. (2012) Cell 150:165-7813; Zhao et al. (2012) Clin Invest 122: 4094-4104).

Example 5—Clinical Treatment Regimen

Treatment with X4P-001 as a monotherapy, or in combination with a checkpoint inhibitor, such as nivolumab, may be performed in cycles, such as on a 2 week, 4 week, 6 week or 8 week cycle. In certain embodiments, the cycle is 4 weeks long. X4P-001 at a determined dose from 200 mg to 1200 mg daily is administered orally either once daily or twice daily in divided doses. Patients are instructed about both dosing schedule and requirements relating to food or drink near the time of dosing.

Dosing Schedule.

The daily dose is taken first thing in the morning. Where the dose is divided, the first daily dose is taken in the morning and the second daily dose approximately 12 hours later using the following guidelines:

Dosing should be at the same time(s) each day ±2 hr.
For twice daily dosing, the interval between successive doses should not be <9 hours nor >15 hours. If the interval would be >15 hrs, the dose should be omitted and the usual schedule resumed at the next dose.
Restrictions relating to food. Absorption is impacted by food and patients will be instructed as follows:
For the morning dose
No food or drink (except water) after midnight until the time of dosing
No food or drink (except water) for 2 hour after dosing.
For the second daily dose, if applicable
No food or drink (except water) for 1 hour before dosing
No food or drink (except water) for 2 hours after dosing.

Nivolumab is administered consistent with prescribed labeling information. Concomitant treatment with X4P-001 and nivolumab may be administered, beginning with daily administration of X4P-001 at day 1. Initial treatment with nivolumab is at 3 mg/kg administered by intravenous infusion over 60 minutes in clinic at the week 4 and 7 visits. Patients may, with the approval of their clinician, vary the dosing schedule or dosage of nivolumab, Dosing of X4P-001 and/or nivolumab may be adjusted by the clinician as appropriate. The dose of X4P-001 and/or nivolumab may be lowered according to the judgment of the clinician. If a patient receiving X4P-001 in combination with nivolumab experiences an adverse event at Grade >2, the dose of X4P-001 and/or nivolumab may be lowered according to the judgment of the clinician. If a patient successfully completes the first 4 weeks of treatment, that is, without experiencing any adverse events greater than Grade 2, the daily dose of X4P-001 and/or nivolumab may be increased, consistent with the judgment of the clinician.

Evaluation of Response to Treatment and Disease Status.

Classification of tumor response may be performed according to codified tumor response evaluation, according to the Response Evaluation Criteria in Solid Tumors Group ("RECIST"), as described in Therasse et al. (2000), J. National Cancer Institute, 92:205-216. Radiologic assessment of ccRCC is accomplished by Computed Tomography (CT) with slice thickness ≤5 mm and contrast. CT is performed prior to treatment (baseline) and may be made at intervals during treatment to determine the response.

Key terminology:
Measurable non-nodal lesions—≥10 mm in longest diameter.
Measurable nodal lesions—≤15 mm in short axis
Nonmeasurable lesions—lesions that are smaller, including those that cannot be measured.
Measurable disease—presence of at least one measurable lesion.
Target Lesions
At baseline, four (4) measureable lesions, two (2) for each individual organ, are identified, documented, and the appropriate diameter of each is recorded. If measurable extra-renal lesions are present, a measurable extra-renal lesion is also identified, documented, and the appropriate diameter is recorded. Lesions are selected based on size, to be representative of disease, and suitable for reproducible repeat measurement. Target lesions may include measurable lymph nodes.

During treatment, each target lesion is assessed for Complete Response, Partial Response, Stable Disease, or Progressive Disease as follows:
Complete Response (CR)
(a) Disappearance of all non-nodal lesions, and
(b) Absence of pathologic lymph nodes[a].
Partial Response (PR)
(a) ≥30% decrease from baseline in the SOD of the target lesions Stable Disease (SD)
(a) Persisting disease that does not meet criteria for either PR or PD Progressive Disease (PD)
a) ≥20% increase in the SOD of the target lesions, compared to the smallest sum, which may be either at baseline or while on treatment; and
(b) an absolute increase of ≥5 mm in the SOD.
Non-Target Lesions
All other lesions present at baseline, including pathologic nodes (defined as nodes >10 mm in short axis) should be documented (quantitative measurements are not required) so that they can be classified on follow-up as present, absent, or unequivocal progression.

Complete Response (CR)
(a) Disappearance of all non-target lesions, and
(b) Absence of pathologic lymph nodes[a].
Non-CR/non-PD
Persistence of one or more non-target lesions
Progressive Disease (PD)
Unequivocal progression of existing non-target lesions.
[Note: a=All lymph nodes, whether or not designated target or non-target lesions, have short axis diameter ≤10 mm]
New Lesions A new lesion should be unequivocal (e.g., not attributable to variation in technique); includes lesions in a location not scanned at baseline.

Pharmacokinetic Assessments

If desired, pharmacokinetic assessment of blood samples for plasma levels of X4P-001 and nivolumab may be conducted. Blood samples are collected as scheduled. Samples are analyzed for X4P-001 concentration using reversed-phase high performance liquid chromatography (RP-HPLC) with MS/MS detection. The validated range of this bioanalytic method is 30 to 3,000 ng/mL in plasma.

Pharmacokinetic assessment of nivolumab may be accomplished using techniques, such as those described in Glassman and Balthasar (2014) Cancer Biol. Med. 11:20-33; Wang et al. (2014), Cancer Immunology Research, 2:1-11; or the Assessment Report of the European Medicines Agency (EMA) for nivolumab EMEA, assessment report EMA/CHMP/76688/2015, Apr. 23, 2015. The full disclosure of these documents are hereby specifically incorporated herein by reference.

REFERENCES

1. Ratajczak, et al. The pleotropic effects of the SDF-1-CXCR4 axis in organogenesis, regeneration, and tumorigenesis. Leukemia 2006:20; 1915-1924.
2. Scala, et al. Expression of CXCR4 predicts poor prognosis in patients with malignant melanoma. Clin Cancer Res 2005:11; 1835-1841.
3. Toyozawa, et al. Chemokine receptor CXCR4 is a novel marker for the progression of cutaneous malignant melanoma. Acta Histochem Cytochem. 2012; 45:293-299.
4. Kim, et al. CXCR4 signaling regulates metastasis of chemoresistant melanoma cells by a lymphatic metastatic niche. Cancer Res. 2010; 70:10411-10421.
5. Mosi R M, Anastassova V, Cox J, et al. The molecular pharmacology of AMD11070: An orally bioavailable CXCR4 HIV entry inhibitor. Biochem Pharmacol. 2012; 83:472-479.
6. D'Alterio, et al. Inhibition of stromal CXCR4 impairs development of lung metastases. Cancer Immunol Immunother. 2012:61; 1713-1720.
7. Feig, et al. Targeting CXCL12 from FAP-expressing carcinoma-associated fibroblasts synergizes with anti-PD-L1 immunotherapy in pancreatic cancer. PNAS 2013; 110:20212-20217.
9. Stone, et al. Multiple-Dose Escalation Study of the Safety, Pharmacokinetics, and Biologic Activity of Oral AMD070, a Selective CXCR4 Receptor Inhibitor, in Human Subjects. Antimicrob Agents Chemother. 2007; 51(7):2351-2358.
10. Moyle, et al. Proof of Activity with AMD11070, an Orally Bioavailable Inhibitor of CXCR4-Tropic HIV Type 1. Clin Infect Dis.2009; 48:798-805.
12. Tumeh, et al. PD-1 blockade induces responses by inhibiting adaptive immune resistance. Nature 2014:515; 568-571.
14. Nyunt, et al. Pharmacokinetic Effect of AMD070, an Oral CXCR4 Antagonist, on CYP3A4 and CYP2D6 Substrates Midazolam and Dextromethorphan in Healthy Volunteers. J Acquir Immune Defic Syndr. 2008; 47:559-565.
15 Cao, et al. Effect of Low-Dose Ritonavir on the Pharmacokinetics of the CXCR4 Antagonist AMD070 in Healthy Volunteers. Antimicrob Agents Chemother. 2008; 52:1630-1634.
16. Common Terminology Criteria for Adverse Events (CTCAE). Version 4.0, 28 May 2009. U.S. Department of Health and Human Services, National Institutes of Health, National Cancer Institute. NIH Publication No. 03-5410.
17 NCI CTCAE v4.03, 14 Jun. 2010 available at (accessed 6 Apr. 2015): http://evs.nci.nih.gov/ftpl/CTCAE/CT-CAE_4.03_2010-06-14_QuickReference_5×7.pdf
18. WMA Declaration of Helsinki—Ethical Principles for Medical Research Involving Human Subjects. Available at (accessed 6 Apr. 2015) http://www.wma.net/en/30publications/10policies/b3/
19. Vanharanta et al. Epigenetic expansion of VHL-HIF signal output drives multiorgan metastasis in renal cancer. Nat Med 2013; 19: 50-6.
20. Gale and McColl, Chemokines: extracellular messengers for all occasions? BioEssays 1999; 21: 17-28.
21. Highfill et al., Disruption of CXCR2-mediated MDSC tumor trafficking enhances anti-PD1 efficacy. Sci Transl Med 2014; 6: ra67.
22. Facciabene et al., Tumour hypoxia promotes tolerance and angiogenesis via CCL28 and Treg cells. Nature 2011; 475: 226-230.
23. Montane et al., Prevention of murine autoimmune diabetes by CCL22-mediated Treg recruitment to pancreatic islets. J Clin Invest 2011; 121: 3024-8.
24. Acharyya et al., CXCL1 paracrine network links cancer chemoresistance and metastasis. Cell 2012; 150: 165-78.
25. Zhao et al., TNF signaling drives myeloid-derived suppressor cell accumulation. J Clin Invest 2012; 122: 4094-4104.
26. Silva et al., Profiling essential genes in human mammary cells by multiplex RNA1 screening. Science 2008; 319: 617-20.
27. Schlabach et al., Cancer proliferation gene discovery through functional genomics. Science 2008; 319: 620-24.
28. Shen et al., CXCR4-mediated STAT3 activation is essential for CXCL12-induced invasion in bladder cancer. Tumour Biol 2013; 34: 1839-45.

I claim:

1. A method for treating a cancer selected from metastatic renal cell carcinoma or metastatic renal cell cancer in a patient in need thereof, wherein said method comprises administering to said patient X4P-001 or a pharmaceutically acceptable salt thereof in combination with nivolumab; wherein the cancer is refractory to nivolumab.

2. The method of claim 1, wherein the cancer is metastatic renal cell carcinoma.

3. The method of claim 1, wherein the patient has previously been treated with an immune checkpoint inhibitor.

4. The method of claim 3, wherein the patient has previously been treated with nivolumab.

5. The method of claim 3, wherein the patient is treated with X4P-001 or a pharmaceutically acceptable salt thereof in an amount effective to increase CD8+ T cell density, and the patient is then treated with nivolumab.

6. The method of claim 5, further comprising the step of obtaining a biological sample from the patient and measuring the amount of a disease-related biomarker.

7. The method of claim 6, wherein the biological sample is a blood sample.

8. The method of claim 7, wherein the disease-related biomarker is circulating CD8+ T cells.

9. The method of claim 3, wherein the X4P-001 or a pharmaceutically acceptable salt thereof is administered orally twice per day.

10. A method for increasing responsiveness to treatment of metastatic renal cell carcinoma or metastatic renal cell cancer with nivolumab in a patient receiving said treatment, said method comprising administering to said patient X4P-001 or a pharmaceutically acceptable salt thereof in an amount effective to increase CD8+ T cell density; wherein the metastatic renal cell carcinoma or metastatic renal cell cancer is refractory to nivolumab.

11. The method of claim 1, wherein the X4P-001 or a pharmaceutically acceptable salt thereof is administered as a unit dosage form comprising a composition comprising:
 (a) X4P-001, or a pharmaceutically acceptable salt thereof in 30-40% by weight of the composition;
 (b) microcrystalline cellulose in 20-25% by weight of the composition;
 (c) dibasic calcium phosphate dihydrate in 30-35% by weight of the composition;
 (d) croscarmellose sodium in 5-10% by weight of the composition;
 (e) sodium stearyl fumarate in 0.5-2% by weight of the composition;
 (f) colloidal silicon dioxide in 0.1-1.0% by weight of the composition; and
 (g) sodium lauryl sulfate in 0.1-1.0% by weight of the composition.

12. The method of claim 11, wherein the unit dosage form is in the form of a capsule.

13. The method of claim 12, wherein the capsule comprises 100 mg X4P-001, or a pharmaceutically acceptable salt thereof.

14. The method of claim 11, wherein the cancer is resectable renal cell carcinoma.

15. The method of claim 14, wherein the patient has undergone surgery for removal of some or all of the renal cell carcinoma.

16. The method of claim 11, wherein the renal cell carcinoma is unresectable.

17. The method of claim 1, wherein the patient has previously received anticancer chemotherapy or immunotherapy.

18. The method of claim 17, wherein the patient has previously received treatment with anti-angiogenic therapy and/or an immune checkpoint inhibitor but not X4P-001 or a pharmaceutically acceptable salt thereof.

19. The method of claim 10, wherein the cancer is metastatic renal cell carcinoma and wherein the X4P-001, or a pharmaceutically acceptable salt thereof, is administered at a daily dose of 200 mg to 600 mg.

20. The method of claim 1, wherein the X4P-001, or a pharmaceutically acceptable salt thereof, is administered at a daily dose of 200 mg to 600 mg.

21. The method of claim 1, wherein the X4P-001, or a pharmaceutically acceptable salt thereof, is administered at a daily dose of 200 mg to 600 mg; and the nivolumab is administered at a dose of 3 mg/kg as an intravenous infusion over 60 minutes every two weeks.

22. The method of claim 1, wherein the X4P-001 is administered at a daily dose of 400 mg.

23. The method of claim 4, wherein the X4P-001, or a pharmaceutically acceptable salt thereof, is administered at a daily dose of 200 mg to 600 mg; and the nivolumab is administered at a dose of 3 mg/kg as an intravenous infusion over 60 minutes every two weeks.

\* \* \* \* \*